United States Patent
Smith et al.

(10) Patent No.: US 9,545,258 B2
(45) Date of Patent: Jan. 17, 2017

(54) TISSUE APERTURE SECURING AND SEALING APPARATUSES AND RELATED METHODS OF USE

(75) Inventors: Paul J. Smith, Smithfield, RI (US); John Golden, Norton, MA (US); Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1321 days.

(21) Appl. No.: 12/078,910

(22) Filed: Apr. 8, 2008

(65) Prior Publication Data
US 2008/0287988 A1 Nov. 20, 2008

Related U.S. Application Data

(60) Provisional application No. 60/924,495, filed on May 17, 2007.

(51) Int. Cl.
| | | |
|---|---|---|
| A61B 17/08 | (2006.01) | |
| A61B 17/128 | (2006.01) | |
| A61B 17/00 | (2006.01) | |
| A61B 17/04 | (2006.01) | |
| A61B 17/064 | (2006.01) | |

(52) U.S. Cl.
CPC ......... *A61B 17/128* (2013.01); *A61B 17/0057* (2013.01); *A61B 17/0469* (2013.01); *A61B 17/0643* (2013.01); *A61B 17/0644* (2013.01); *A61B 2017/00637* (2013.01); *A61B 2017/00663* (2013.01); *A61B 2017/047* (2013.01)

(58) Field of Classification Search
CPC ................. A61B 17/0057; A61B 2017/00584; A61B 2017/0061; A61B 2017/00668; A61B 2017/00676
USPC ................................ 606/151, 213, 232, 219
See application file for complete search history.

(56) References Cited

U.S. PATENT DOCUMENTS

| | | |
|---|---|---|
| 3,874,388 A | 4/1975 | King et al. |
| 5,236,440 A | 8/1993 | Hlavacek |
| (Continued) | | |

FOREIGN PATENT DOCUMENTS

| | | |
|---|---|---|
| EP | 1 454 587 A2 | 9/2004 |
| EP | 1 595 504 A1 | 11/2005 |
| WO | WO 01/21246 A1 | 3/2001 |

OTHER PUBLICATIONS

Communication Relating to the Results of the Partial International Search in PCT/US2008/063714 (Annex to PCT/ISA/206—Invitation to Pay Additional Fees dated Oct. 20, 2008), 2 pages.

(Continued)

*Primary Examiner* — Gregory Anderson
*Assistant Examiner* — Christina Lauer
(74) *Attorney, Agent, or Firm* — Bookoff McAndrews, PLLC

(57) ABSTRACT

Embodiments of the invention are directed to apparatuses for securing and sealing apertures in tissue and related methods of use. An exemplary apparatus for collapsing an aperture in a wall of tissue can include a base biased to collapse into a collapsed state from an expanded state. The apparatus can also include a plurality of collapsible fingers extending from the base, wherein the collapsible fingers can be configured to collapse about tissue adjacent to and defining the aperture so as to close the aperture in the wall of tissue.

44 Claims, 16 Drawing Sheets

(56) References Cited

U.S. PATENT DOCUMENTS

| | | | | |
|---|---|---|---|---|
| 5,478,353 | A | * | 12/1995 | Yoon .............................. 606/213 |
| 5,531,760 | A | | 7/1996 | Alwafaie |
| 5,944,730 | A | * | 8/1999 | Nobles et al. ................. 606/151 |
| 6,030,395 | A | * | 2/2000 | Nash et al. .................... 606/153 |
| 6,355,052 | B1 | * | 3/2002 | Neuss et al. ................... 606/213 |
| 6,645,205 | B2 | * | 11/2003 | Ginn .................. A61B 17/0644 128/200.24 |
| 2003/0153946 | A1 | * | 8/2003 | Kimblad ....................... 606/213 |
| 2004/0097993 | A1 | * | 5/2004 | Whayne ........................ 606/153 |
| 2004/0220592 | A1 | * | 11/2004 | Mueller et al. ............... 606/151 |
| 2005/0283188 | A1 | * | 12/2005 | Loshakove ........ A61B 17/0057 606/213 |
| 2006/0271103 | A1 | | 11/2006 | Ferrari et al. |
| 2007/0198058 | A1 | | 8/2007 | Gelbart et al. |
| 2007/0225797 | A1 | * | 9/2007 | Krivoruhko ................. 623/1.35 |

OTHER PUBLICATIONS

International Search Report for PCT/US2008/063714 dated Jan. 14, 2009.
Written Opinion of the International Searching Authority for PCT/US2008/063714 dated Jan. 14, 2009.

* cited by examiner

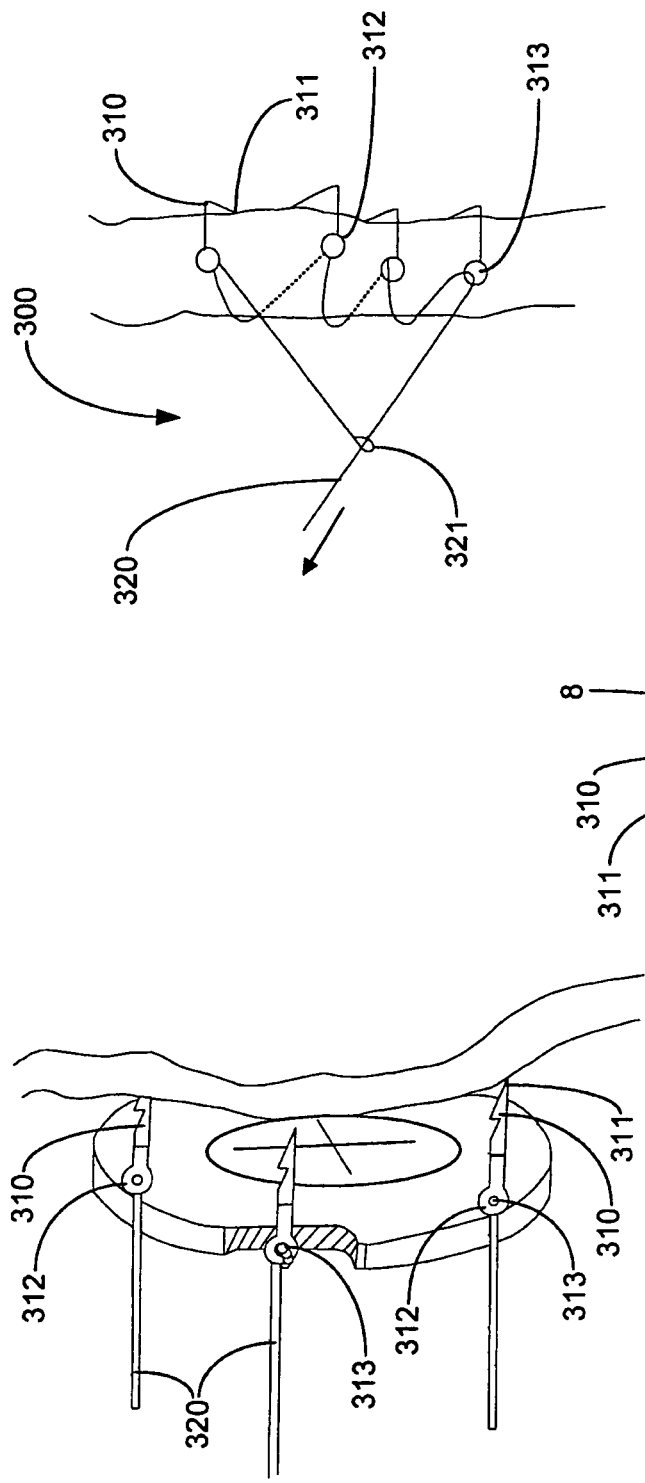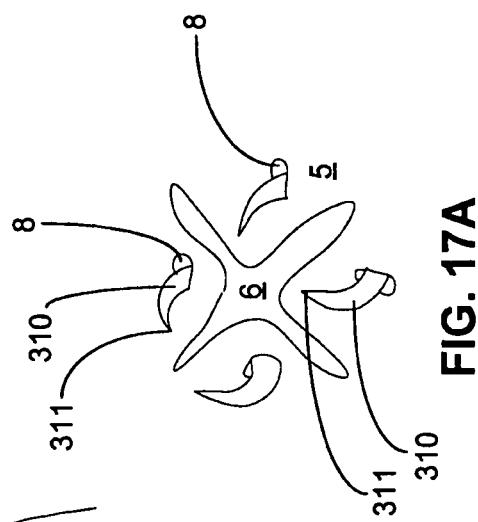
FIG. 17
FIG. 17A
FIG. 16

TISSUE APERTURE SECURING AND SEALING APPARATUSES AND RELATED METHODS OF USE

CROSS-REFERENCE TO RELATED APPLICATION

This patent application claims the benefit of priority under 35 U.S.C. §119 to U.S. Provisional Patent Application No. 60/924,495, entitled TISSUE APERTURE SECURING AND SEALING APPARATUSES AND RELATED METHODS OF USE, filed on May 17, 2007, the entirety of which is incorporated herein by reference.

DESCRIPTION OF THE INVENTION

Field of the Invention

Embodiments of the invention may be directed to apparatuses for securing and sealing apertures in tissue and related methods of use.

Background of the Invention

Medical devices and procedures are used to treat internal body organs of a patient. One method of treating internal body organs includes open surgery where the internal body organs are exposed to the outside environment. Such procedures are invasive, expensive, time consuming, and may have a high risk of infection.

Another method includes procedures where apertures are formed in a body lumen adjacent to a body cavity. Medical devices are then advanced from the body lumen, through the aperture, and into the body cavity where medical procedures are performed.

SUMMARY OF THE INVENTION

An embodiment of the invention may include an apparatus for collapsing an aperture in a wall of tissue. The apparatus may include a base and a plurality of collapsible fingers extending from the base. The collapsible fingers may be configured to collapse about tissue adjacent to and defining the aperture so as to close the aperture in the wall of tissue.

Various embodiments of the invention may include one or more of the following aspects: the base may define a gap in an expanded state of the base, the base further having a collapsed state without the gap; an assembly including any apparatus set forth herein and a delivery apparatus; the delivery apparatus may include an elongate flexible member and a distal assembly connected to the elongate flexible member; the distal assembly may be configured to accommodate the apparatus; the base may define an aperture for receiving the distal assembly therethrough; the distal assembly may include a distal tip configured to puncture the wall of tissue and form the aperture; the distal assembly may include a member and a stepped portion configured to accommodate the base; a cross-sectional area of the stepped portion may be larger than a cross-sectional area of the member immediately proximal to the stepped portion; an outer surface of the base may lie essentially flush with a surface of the distal assembly that is distal to the stepped portion; the distal assembly may include at least one strand connected to the base; the at least one strand may be configured to assist in positioning the apparatus about the aperture to be closed; the at least one strand may be connected to the distal assembly; a distal end of the elongate member may include a notch configured to accommodate the at least one strand therethrough; the notch may be configured to allow the at least one strand to assist in deploying the base about the distal end of the elongate member; at least a portion of the base may be configured to overlap with another portion of the base; and at least some of plurality of fingers may be configured to overlap others of the plurality of fingers.

Another embodiment of the invention may include method of closing an aperture in a wall of tissue. The method may include providing an apparatus including a base and a plurality of collapsible fingers extending from the base, providing a delivery apparatus including an elongate member, advancing the apparatus through the body lumen via the delivery apparatus, expanding the apparatus around the aperture, and collapsing the apparatus about tissue adjacent to and defining the aperture so as to close the aperture.

Various embodiments of the invention may include one or more of the following aspects: the delivery apparatus may include a distal assembly, the apparatus being disposed about the distal assembly; during the step of expanding the apparatus a gap is formed in the base; the base may define an aperture for receiving the distal assembly therethrough; forming the aperture by advancing a distal tip of the distal assembly through the wall of tissue; the distal assembly may include a member and a stepped portion configured to accommodate the base; a cross-sectional area of the stepped portion may be larger than a cross-sectional are of the member immediately proximal to the stepped portion; expanding the base so as to move the base over and distal to the stepped portion; the distal assembly may include at least one strand connected to the base; placing a proximal force on the at least one strand so as to assist in positioning the apparatus about the aperture to be closed; the at least one strand may be connected to the distal assembly; retracting the distal assembly in the proximal direction so as to place the proximal force on the at least one strand; a distal end of the elongate member may include a notch configured to accommodate the at least one strand therethrough; placing the at least one strand in the notch; deploying the base about the distal end of the elongate member; detaching the at least one strand from the base so as to collapse the apparatus; overlapping at least a portion of the base with another portion of the base; and overlapping at least some of plurality of fingers with others of the plurality of fingers.

A further embodiment of the invention may include a method of closing an aperture in a wall of tissue. The method may include providing an apparatus including an elongate member including a first end and a second end, each of the first end and the second end including a hook, advancing the apparatus to a first side of the wall, advancing the first and second ends through the aperture to a second side of the wall, after advancing the first and second ends through the aperture, advancing the first and second ends through the wall to the first side of the wall, and coupling the first and second ends together so as to close the aperture.

Various embodiments of the invention may include one or more of the following aspects: the apparatus may include a plurality of apparatuses; coupling may include tying; the first and second ends may each form individual apertures on substantially opposite sides of the aperture; providing a tool for use with the apparatus, the tool including a distal assembly configured to accommodate the hooks of the apparatus in a substantially straight configuration; advancing at least a portion of the distal assembly through the aperture; the step of advancing the first end through the wall includes advancing the first end out of the distal assembly such that the hook reverts to a hooked configuration; the distal assembly may define a plurality of inner channels, the plurality of inner channels being substantially parallel to a longitudinal axis of the distal assembly; the hook may be disposed in the one of the plurality of inner channels in a substantially straight configuration; at least one of the elongate member and the distal assembly may define a plurality of slots; and the step of advancing the first end out of the distal assembly may include advancing the first end out of one of the plurality of slots.

Yet another embodiment of the invention may include an apparatus. The apparatus may include an elongate member, a distal assembly connected to the elongate member, a plurality of inner channels defined by the distal assembly, the plurality of inner channels being substantially parallel to a longitudinal axis of the distal assembly, a plurality of slots defined by at least one of the elongate member and the distal assembly, and a hook disposed in one of the plurality of inner channels, the hook being disposed in the one of the plurality of inner channels in a substantially straight configuration. The distal assembly may be configured so that the hook may be advanced out of the one of the plurality of inner channels through one of the plurality of slots.

A yet further embodiment of the invention may include an apparatus. The apparatus may include a plurality of hooks configured to be disposed in a wall of tissue, at least one strand connecting the plurality of hooks, and a tool configured to detachably accommodate the plurality of hooks, the tool including a perforation configured to accommodate a medical device therethrough.

Various embodiments of the invention may include one or more of the following aspects: the perforation may be biased toward a closed configuration when not accommodating a medical device therethrough; the tool may include a septum with a slit, the slit being configured to accommodate the medical device therethrough; the plurality of hooks may be disposed around the perforation when the plurality of hooks are attached to the tool; the at least one strand may connect the plurality of hooks such that when the plurality of hooks are disposed in the wall of tissue, placing a proximal force on the at least one strand causes the plurality of hooks to move closer together; and a portion of the plurality of hooks may be detachably secured to a plurality of apertures in the tool.

Still another embodiment of the invention may include a method of closing an aperture in a wall of tissue. The method may include providing a plurality of hooks, distally advancing the plurality of hooks through a body and embedding each of the plurality of hooks in a wall of tissue around an aperture, connecting the plurality of hooks via a strand, and placing a proximal force on the strand so as to bring the plurality of hooks closer together and close the aperture.

Various embodiments of the invention may include one or more of the following aspects: providing a tool; the plurality of hooks may be detachably attached to a distal end of the tool; after the step of embedding, detaching the plurality of hooks from the distal end of the tool; the tool may include a perforation configured to accommodate a medical device therethrough; biasing the perforation toward a closed configuration when not accommodating the medical device therethrough; the tool may include a septum with a slit; the slit may be configured to accommodate the medical device therethrough; and a portion of the plurality of hooks may be press-fit into a plurality of apertures in the tool.

A still further embodiment of the invention may include a method of closing an aperture in a wall of tissue. The method may include providing an apparatus including a plurality of hooks, each of the hooks being connected to an elongate member, distally advancing the apparatus to a first side of the wall, distally advancing each of the plurality of hooks through the aperture to a second side of the wall, after advancing each of the plurality of hooks through the aperture, advancing each of the plurality of hooks through the wall to the first side of the wall, placing the plurality of elongate members through a connector, and proximally advancing the plurality of elongate members through the connector so as to bring the plurality of hooks closer together and close the aperture.

Various embodiments of the invention may include one or more of the following aspects: the connector may include a portion of the elongate member of one of the hooks, after the step of proximally advancing the plurality of elongate members, placing a collar around at least some of the plurality of elongate members at a location proximal to the connector; the step of proximally advancing the plurality of elongate members may include proximally advancing at least some of the plurality of elongate members in substantially the same direction; and the step of proximally advancing the plurality of elongate members may include proximally advancing at least some of the plurality of elongate members in different directions.

Another embodiment of the invention may include a method of closing an aperture in a wall of tissue. The method may include providing a strand in a preformed configuration including a plurality of loops, distally advancing the strand to a first side of the wall, through an aperture in the wall, to a second side of the wall, proximally retracting the plurality of loops of the strand, through a plurality of individual apertures, from the second side of the wall to the first side of the wall, and placing a proximal force on at least some of the plurality of loops so as to shorten a length of the strand disposed on the second side of the wall and close the aperture. The plurality of individual apertures may be disposed around the aperture.

Various embodiments of the invention may include one or more of the following aspects: the preformed configuration may include a square knot, providing a tool including a distal end having a plurality of hooks, placing the plurality of loops on the plurality of hooks, and proximally advancing the tool so as to place the proximal force on the strand; providing an elongate member configured to accommodate the strand in the preformed configuration; step of distally advancing may include distally advancing the strand via the elongate member; during the step of distally advancing, the strand may be disposed within the elongate member; during the step of distally advancing, the strand may be removably attached to an exterior surface of the elongate member; and wherein in the preformed configuration the plurality of loops may be disposed in a substantially proximal direction.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 14-17 and 17A depict an apparatus, a tool for use with the apparatus, and methods of using both the tool and the apparatus, according to yet another embodiment of the invention;

DESCRIPTION OF THE EMBODIMENTS

Figure 1:
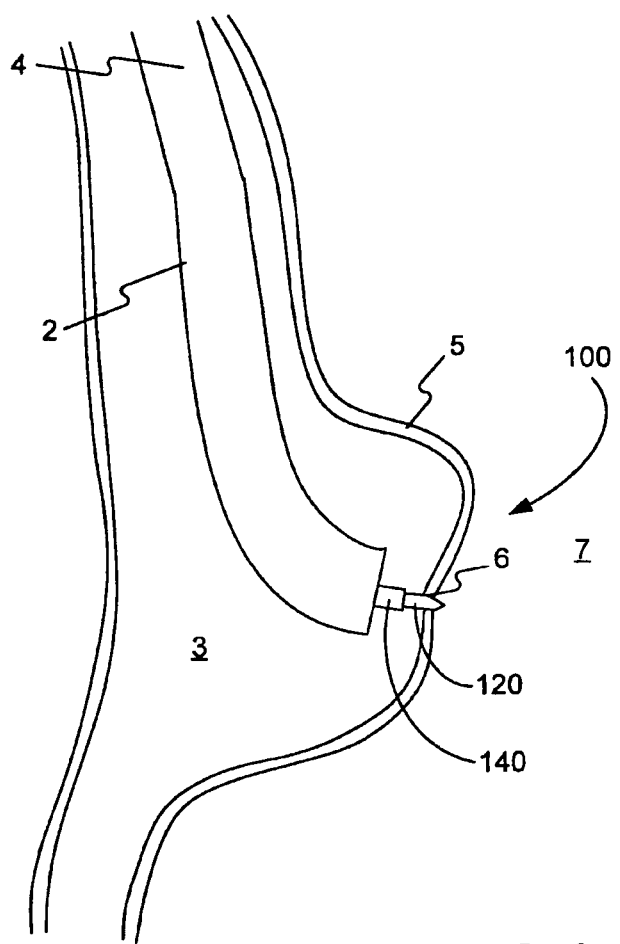
FIGS. 1-11 depict apparatuses and methods of using the apparatus, according to embodiments of the invention.
Figure 2:
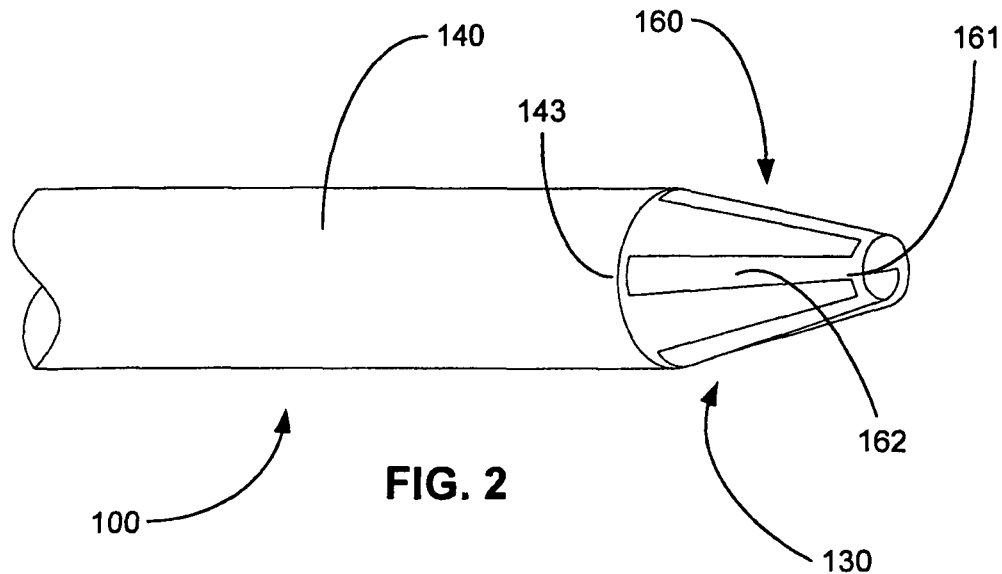
Figure 3:
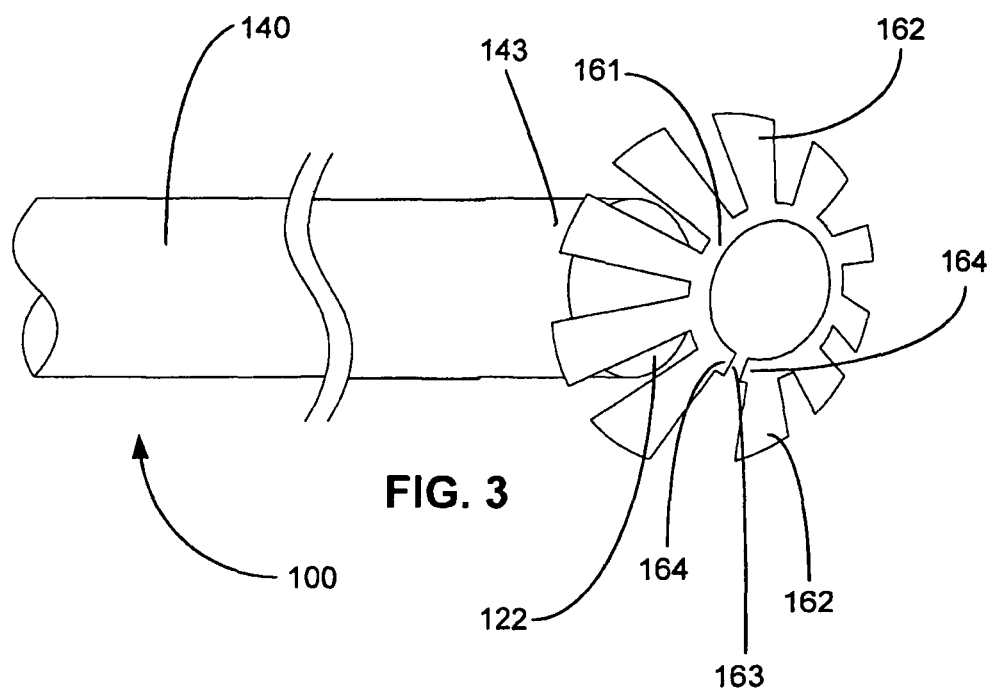
Figure 4:
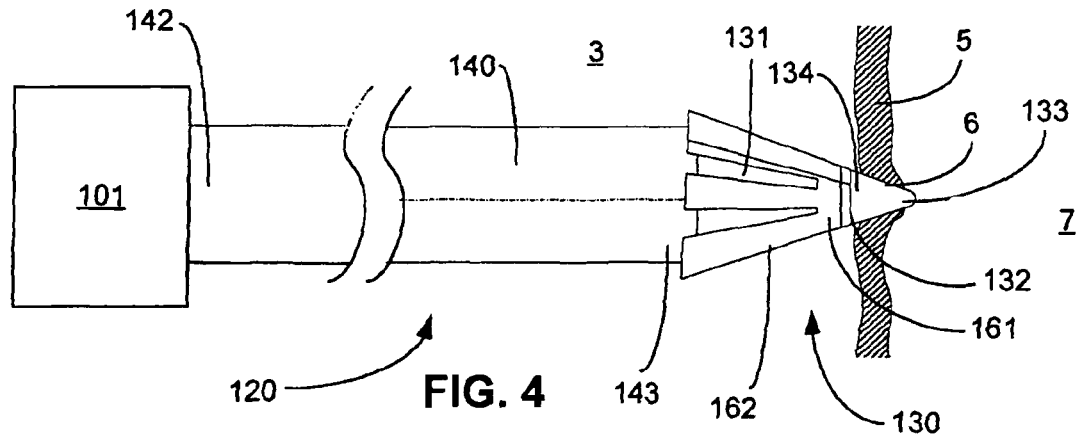

Reference will now be made in detail to exemplary embodiments of the invention, examples of which are illustrated in the accompanying drawings. Wherever possible, the same reference numbers will be used throughout the drawings to refer to the same or like parts.

An embodiment of the invention may include an apparatus 100. Apparatus 100 may include handle portion 101, deployment mechanism 120, elongate member 140, and retractor 160, for example, as shown in FIGS. 1-11.

Deployment mechanism 120 may include an elongate member 121 connected to a distal assembly 130. Elongate member 121 may be disposed in elongate member 140. Elongate member 121 may define a lumen 122 and may be made out of any suitable material, for example, a flexible material configured to allow elongate member 121 to be advanced through tortuous body lumens such as GI tract 3. Elongate member 121 may include a proximal end connected to a handle portion 101 and a distal end 124 connected to distal assembly 130.

Figure 6:
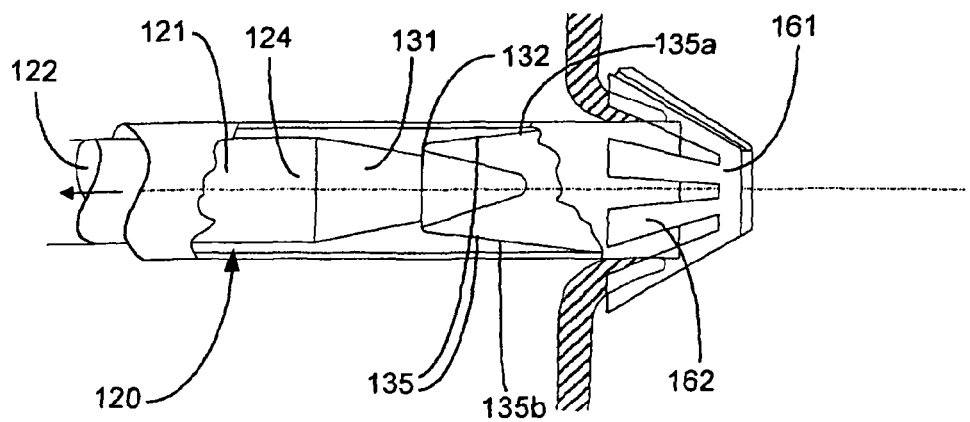
Figure 7:
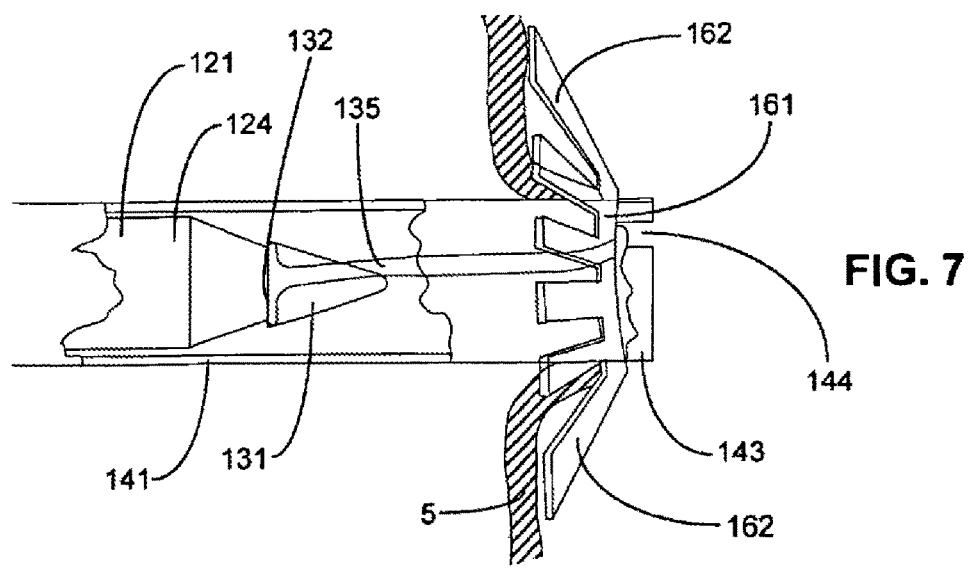
Figure 8:
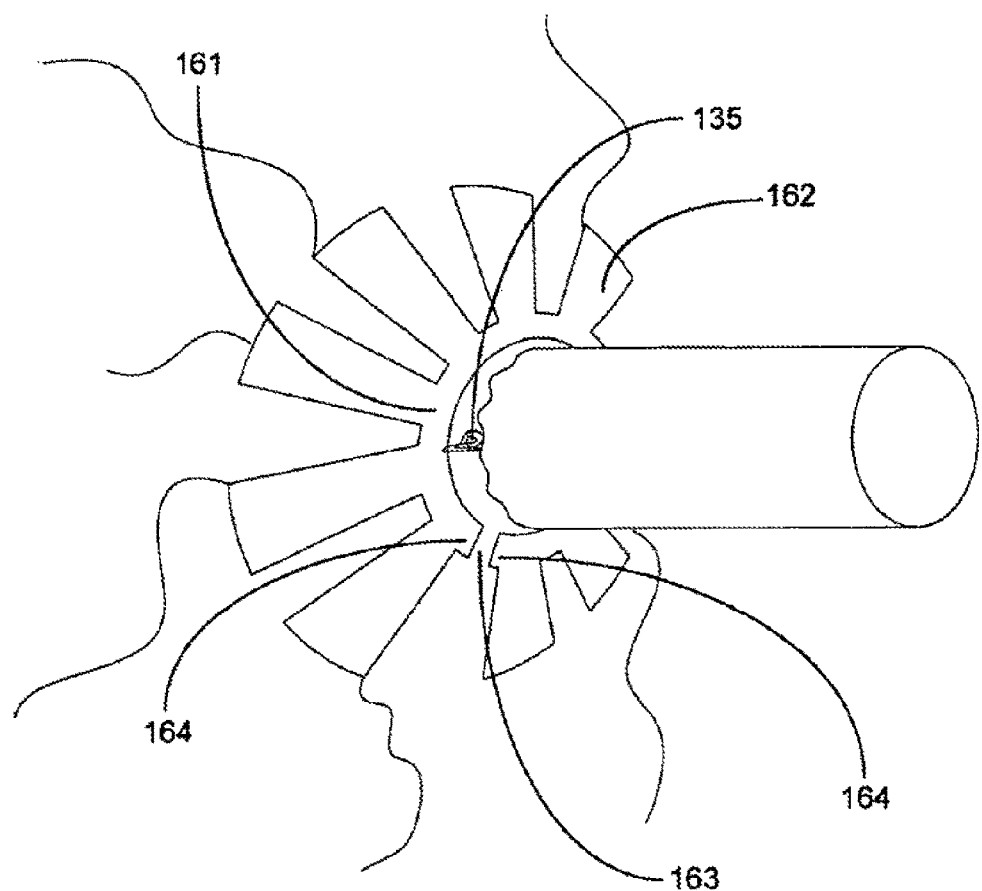

Distal assembly 130 may include member 131. Member 131 may have a cone-like configuration. Member 131 may be configured to pierce tissue and form perforation 6, for example, using distal tip 133. Distal tip 133 may be sufficiently sharp so as to pierce wall 5 of GI tract 3. A proximal end of member 131 may be attached to distal end 124 of elongate member 121 using any suitable method and/or mechanism. Member 131 may include a stepped portion 132. As shown in FIG. 6, stepped portion 132 may be configured such that a cross-sectional area of stepped portion 132 may be larger than a cross-sectional area of a portion of member 131 immediately proximal to stepped portion 132. Stepped portion 132 may be configured to accommodate base 161 of retractor 160, for example to prevent retractor 160 from becoming distally dislodged from distal assembly 130 during advancement of apparatus 100 through a body lumen and aperture 6. Additionally, the stepped configuration of member 131 allows retractor 160 to lay substantially flush with member 131.

Distal assembly 130 may also include at least one strand 135 which may be connected, at opposite ends, to interior member 131 and retractor 160 in any suitable manner using any suitable mechanism. For example, distal assembly 130 may include two strands 135a, 135b disposed on substantially opposite sides of stepped portion 132. Each strand 135 may be configured to be selectively detached from retractor 160, for example, sufficient force placed on strand 135 away from retractor 160 may cause strand 135 to detach from retractor 160. In some embodiments, strand 135 may be configured as a strip of material, such as, for example, a polymer. In one example, strand 135 may be an elastomeric material configured to snap when stretched a sufficient amount. In a further example, strand 135 may be connected to base 161 of retractor 160 via an adhesive. In yet another example, strand 135 may be severed by a notch 144, as will be described. Strand 135 may be made out of a material having sufficient strength, however, to assist in expanding retractor 160 from a collapsed configuration to an expanded configuration.

Elongate member 140 may define a lumen 141. Lumen 141 may be configured to accommodate a medical device therethrough, for example, member 131 of distal assembly 130 and elongate member 121 of deployment mechanism 120. Elongate member 140 may be made out of any suitable material, for example, a flexible material configured to allow elongate member 140 to be advanced through tortuous body lumens such as GI tract 3. Elongate member 140 may include a proximal end 142 connected to handle portion 101 and a distal end 143. Distal end 143 may be configured to accommodate a portion of retractor 160, for example, base 161 of retractor 160 may be disposed around distal end 143. Distal end 143 may include at least one notch 144. Notch 144 may be configured to accommodate strand 135 of distal assembly 130 therein. Notch 144 may be configured to assist strand 135 in deploying retractor 160 from a collapsed configuration to an expanded configuration. For example, when strand 135 places a proximal force on base 161 of retractor 160, base 161 will move proximally until base 161 contacts distal end 143. Due to the geometry of base 161 and strand 135, base 161 can go no further proximally relative to distal end 143. When strand 135 is deployed within notch 144, however, strand 135 may then proximally pull base 161 over and onto distal end 143. Some of wall 5 may be disposed between base 161 and distal end 143 in such a configuration. Notch 144 may also be configured to sever strand 135, for example, by having a sharp proximal edge. Distal end 143 may be configured to have a portion of wall 5 attached and/or wrapped around it, for example, via retractor 160.

Retractor 160 may be configured to have a collapsed configuration and an expanded configuration. In the collapsed configuration, retractor 160 may be configured to be disposed around one or more of distal assembly 130 and distal end 143 of elongate member 140. In the expanded configuration, retractor 160 may be configured to hold a portion of wall 5 around distal end 143 of elongate member 140.

Retractor 160 may be made out of any suitable material to allow it to be moved between the collapsed and expanded configurations, for example, by being at least partially made of spring steel or a shape memory material such as nitinol. Retractor 160 may also have any suitable shape, parts, and/or configurations to accomplish the objectives set forth herein.

Retractor 160 may include a generally circular shaped base 161 including a plurality of fingers 162 extending away from base 161. Base 161 may have a gap 163 separating ends 164 of base 161 in certain configurations, for example, in the expanded configuration of retractor 160. In the collapsed configuration, ends 164 may overlap with other portions of base 161, for example, so as to cause base 161 to have a smaller diameter. Base 161 may be configured to be nestled up against stepped portion 132 of member 131 and flush with outer surface portion 132, for example, when retractor 160 is being advanced through GI tract 3 and through aperture 6.

Fingers 162 may generally extend in the same direction relative to base 161, for example, in a proximal direction. Fingers 162 may be configured to generally splay out away from a longitudinal axis of retractor 160 and may be biased so as to collapse toward the longitudinal axis. Fingers 162 may have any suitable shape, dimensions, and/or configuration. In the collapsed configuration of retractor 160, some of fingers 162 may overlap.

Retractor 160 may be connected to strands 135a, 135b, for example, at base 161 in any suitable manner using any suitable mechanism. Strand 135 may be connected to base 161 in a manner such that proximal force on strand 135 may cause fingers 162 to expand if fingers 162 are placed up against wall 5, and additional proximal force may cause strand 135 to sever from base 161.

Another embodiment of the invention may include a method of using apparatus 100, for example, as shown in FIGS. 1-11. In such a method, apparatus 100 may be provided with retractor 160 in a collapsed configuration about distal assembly 130 and distal end 143 of elongate member 140. Base 161 may be nestled proximal to stepped portion 132 of member 131. Distal tip 133 of member 131 may be disposed distal to base 161 of retractor 160. Retractor 160 may be configured to substantially stay in the collapsed configuration about member 131, for example, due to its inherent inward biasing. Fingers 162 may be disposed about a portion of member 131. Ends of fingers 162 may also be disposed around distal end 143 of elongate member 140. Some of fingers 162 and/or ends 164 of base 161 may overlap.

Figure 5:
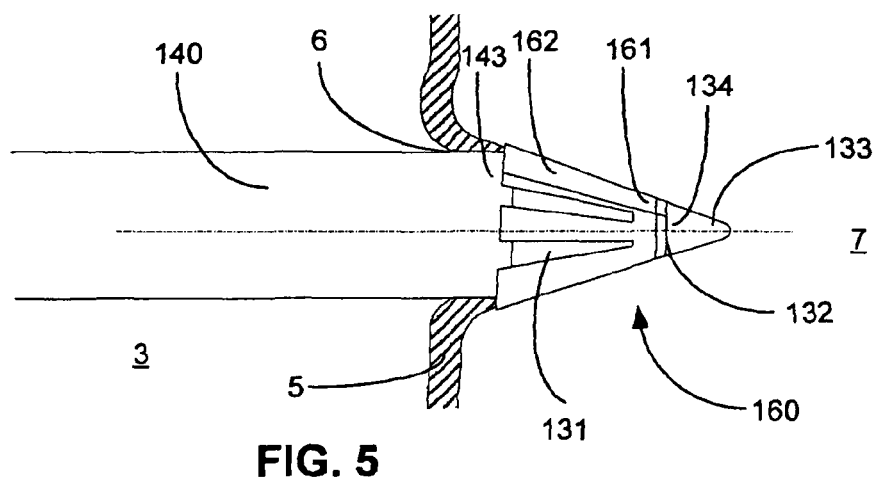

In such a configuration, apparatus 100 may be advanced through lumen 4 of endoscope 2 and into GI tract 3. In the alternative, apparatus 100 may be advanced through GI tract 3 independent of an endoscope 2 or other device. Apparatus 100 may also include optical components. Distal tip 133 may be advanced to the appropriate portion of wall 5 where aperture 6 is desired. Distal tip 133 may then be advanced through wall 5, piercing wall 5, and then may continue to be advanced until substantially all of retractor 160 has been advanced through wall 5 and is disposed in body cavity 7, for example, as shown in FIG. 5. Stepped portion 132 may prevent retractor 160 from distally dislodging during this process.

Once so deployed, member 131 may begin to move proximally into lumen 141. When this happens, enough proximal pressure may be placed on base 161 that base 161 expands slightly. Expansion of base 161 then permits base 161 to move distally past and over stepped portion 132. Some combination of proximal movement of member 131 into lumen 141 of elongate member 140 and a proximal force placed on base 161 via strand 135 (or strands 135a, 135b) may cause fingers 162 to begin to splay out and cease to be disposed around distal end 143. Continued proximal movement of member 131 and force applied by strand 135 causes fingers 162 to come into contact with portions of wall 5 disposed around distal end 143 of elongate member 140. Such movement of fingers 162 slightly in a proximal direction and outward increases the cross-sectional area of retractor 160. At some point in the expansion of retractor 160, fingers 162 and/or ends 164 of base 161 may cease to overlap and gap 163 may be formed between ends 164. As mentioned, base 161 will continue to be moved slightly proximally, for example, via a proximal force from strand 135 attached to base 161, until base 161 is adjacent to distal end 143. At this point, strand 135 may become disposed in notch 144 so as to pull base 161 proximal to distal end 143, and allow base 161 to be disposed around the aforementioned portion of wall 5 and distal end 143. Where notch 144 not present, some other means may be necessary to move base 161 from distal to distal end 143 to around distal end 143. Strand 135 may then be detached from base 161 using any suitable method, for example, strand 135 may be made of an elastomeric material which severs at a sufficient length, strand 135 may be attached to base 161 using adhesives which allows strand 135 to detach when a certain amount of force is placed upon it, and/or notch 144 may include a sharp edge that severs strand 135.

Figure 9:
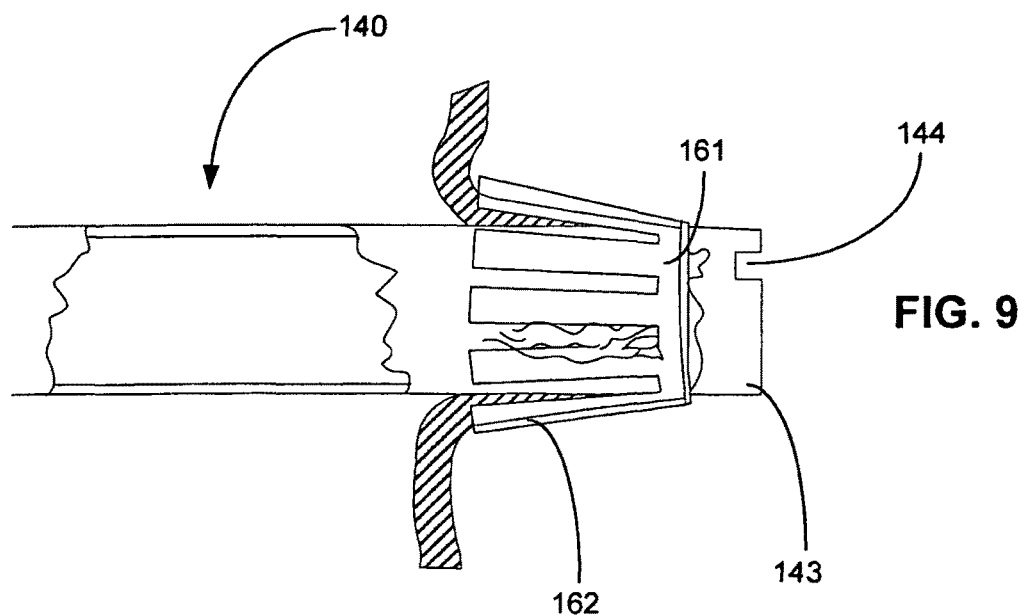

Once proximal movement of retractor 160 has ceased, distal end 143 may be advanced distally further into body cavity 7. When this occurs, more of wall 5 may be disposed around a greater portion of elongate member 140 proximal to distal end 143. Fingers 162 and a portion of base 161 may, due to its natural inward biasing, contract so as to press those portions of wall 5 against elongate member 140, for example, as shown in FIG. 9. Distal end 143 may be distally advanced until wall 5 is sufficiently attached to elongate member 140, for example, when wall 5 adjacent to a proximal end of fingers 162 is physically in contact with elongate member 140. Fingers 162 may exert inward pressure on that portion of wall 5 disposed around elongate member 140. One or more medical instruments may then be advanced through lumen 141, out distal end 143, and into body cavity 7 so as to perform any suitable medical procedures.

In some circumstances, apparatus 100 may be advanced to wall 5 through environments, such as, for example, GI tract 3, containing one or more substances. In these circumstances, it may be desirable to maintain the sterility of lumen 141 relative to GI tract 3, such that substances disposed on, for example, a portion (e.g., an outer surface of distal tip 133) of member 131 are not introduced into lumen 141 and, consequently, body cavity 7 via instruments passed through lumen 141. The sterility of lumen 141 relative to the substances disposed on portions of member 131 may be maintained by any suitable methods known in the art. In one embodiment, it is contemplated that portions of member 131, such as, for example, the distal tip 133, which may have been in contact with substances disposed in GI tract 3, may be prevented from coming into contact with any portion of lumen 141. Preventing contamination of lumen 141 may be achieved by, for example, configuring portions of member 131, such as, for example, distal tip 133, to invert as member 131 exerts pressure on base 161 when member 131 is moved proximally into lumen 141. In such embodiments, member 131 may be made of a material that facilitates inversion of select portions of member 131, as member 131 is being withdrawn into lumen 141.

Figure 10:
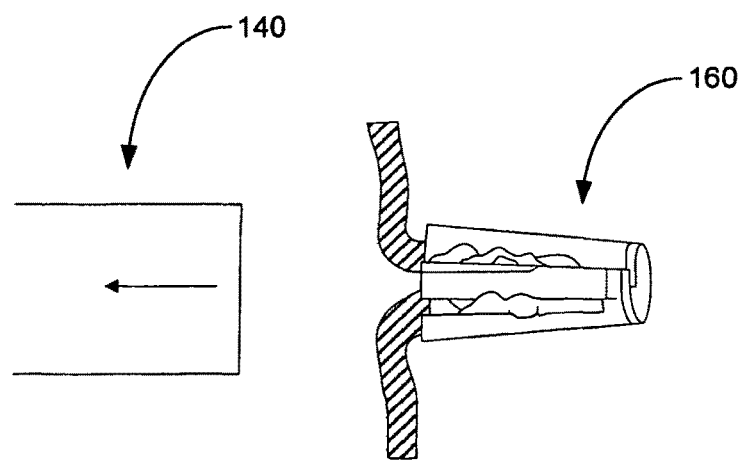
Figure 11:
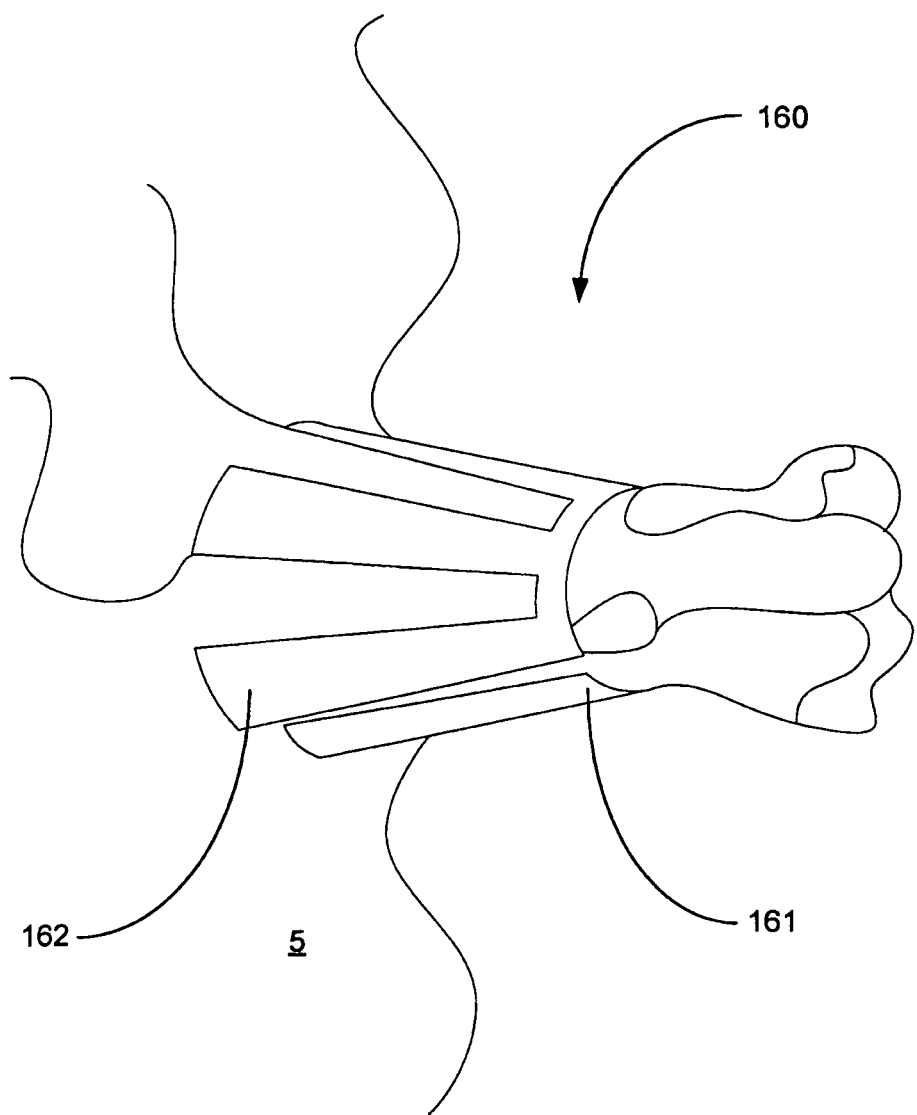

Once all medical procedures have been completed and all medical instruments have been retracted proximally into lumen 141, elongate member 140 may be moved proximally out of body cavity 7, out of aperture 6, and into GI tract 3. When this occurs, retractor 160 disposed around wall 5 and elongate member 140 may collapse so as to close aperture 6. For example, fingers 162 and/or ends 164 of base 161 may overlap so as to collapse the wall around aperture 6 and thus may close aperture 6, for example, as shown in FIGS. 10, 11, leaving retractor 160 disposed within body cavity 7. In another example, inward biasing of retractor 160 and/or portions of retractor 160 may cause retractor 160 to close aperture 6. Aperture 6 may then heal and retractor 160 may be left in the body as it is biocompatible or bioresorbable, or may be moved at any point in time using any suitable method.

Figure 10A:
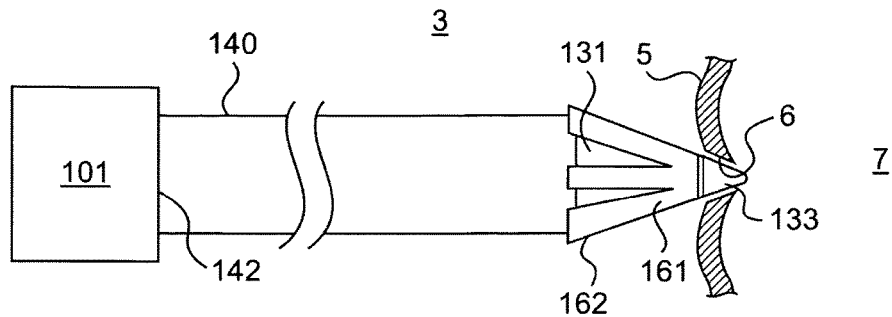
Figure 10B:
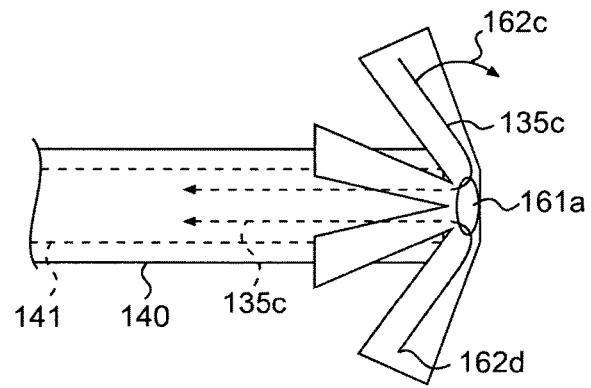
Figure 10C:
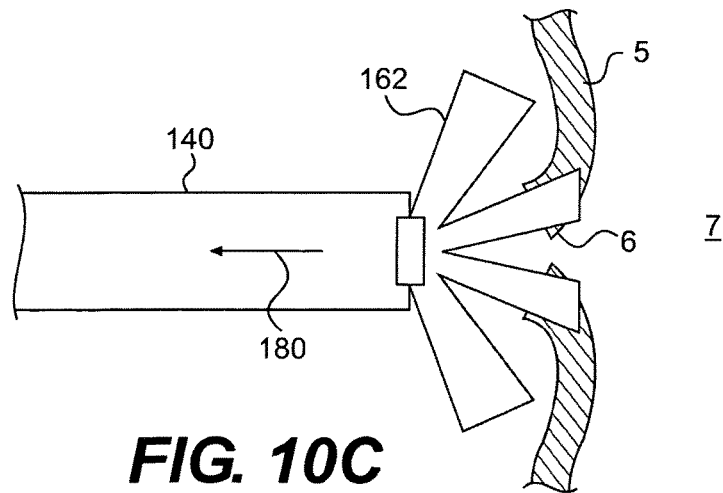

In another embodiment, the retractor 160 may be used to close an aperture 6 in a tissue wall 5. As shown in FIGS. 10A-10C, retractor 160 may be disposed about member 131 in substantially the same manner as described above in connection with FIG. 4. In use, retractor 160 may be advanced through a patient's body to a desired aperture 6 for closing aperture 6. Once positioned proximate aperture 6, an actuator 135*c* may be actuated to expand retractor 160 by moving one or more fingers 162 in the direction shown by arrow 162*c*.

Actuators 135*c* may include any suitable actuator known in the art. For example, actuator 135*c* may include a strand having a distal end 162*d* secured to a finger 162. In some embodiments, a plurality of actuators 135*c* may be provided. Although the depicted embodiment illustrates two actuators 135*c*, those having ordinary skill in the art will readily appreciate that a greater or lesser number of actuators 135*c* may be provided. For example, it is contemplated that the number of actuators 135*c* may correspond to the number of fingers 162 on retractor 160, so as to facilitate moving each of fingers 162 as described above. In other embodiments, a single actuator 135*c* may be configured to move all of the fingers 162 of a retractor 160. For example, a single actuator 135*c* may be provided with a plurality of distal attachment mechanisms (not shown) for attaching actuator 135*c* to each of fingers 162.

As discussed above, actuator 135*c* may be actuated to expand retractor 160 from the collapsed configuration depicted in FIG. 10A, through the partially expanded configuration depicted in FIG. 10B, to the expanded configuration depicted in FIG. 10C. Additionally, continual actuation of actuator 135*c* may cause retractor 160 to collapse in an inverted configuration about portions of wall 5 that surround aperture 6, so as to collapse the wall 5 around aperture 6, and thus, may close aperture 6, for example, as shown in FIG. 10D.

In some instances, the portions of wall 5 surrounding aperture 6 may not be oriented in a manner conducive to collapsing retractor 160 about the wall 5 surrounding aperture 6 for closing aperture 6. In these instances, it may be desirable to draw the portions of wall 5 that surround aperture 6 toward a center portion (e.g., hole 161*a*) of retractor 160, to facilitate collapsing retractor 160 on the portions of wall 5 that surround aperture 6. The portions of wall 5 that surround aperture 6 may be drawn toward a center portion of retractor 160 by any suitable means known in the art. For example, sufficient suction may be applied (through hole 161*a*) in the direction illustrated by arrow 180, as shown in FIG. 10C, to the portions of wall 5 that surround aperture 6 to draw those portions toward a center portion of retractor 160.

Figure 10D:
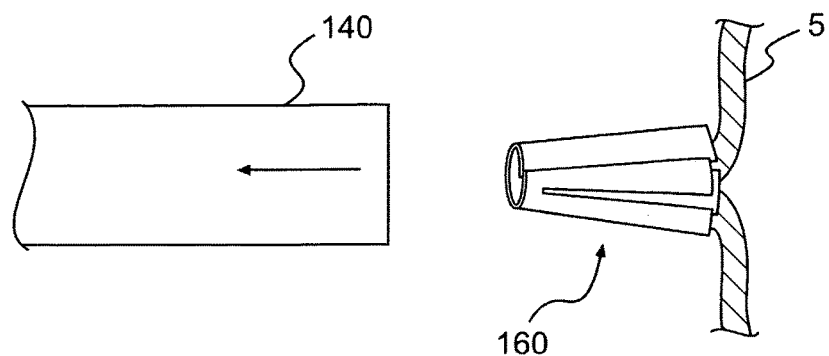

Once retractor 160 is secured to tissue 5, as shown in, for example, FIG. 10D, elongate member 140 may be withdrawn proximally and out of the patient's body. Aperture 6 may then heal and retractor 160 may be left in the body as it is biocompatible or bioresorbable, or may be removed at any point in time using any suitable means.

Figure 10E:
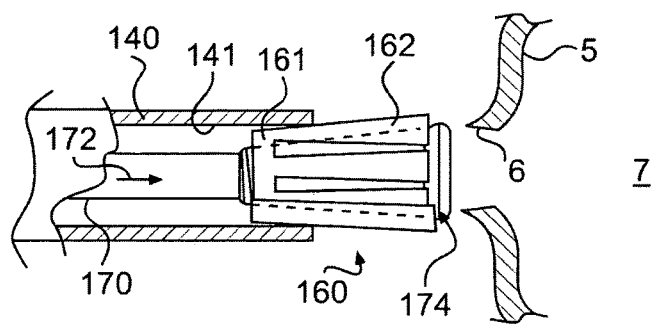
Figure 10F:
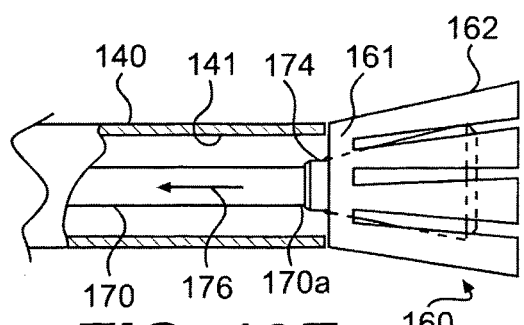
Figure 10G:
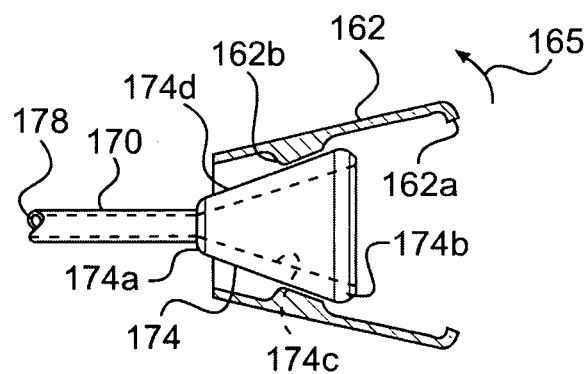
Figure 10H:
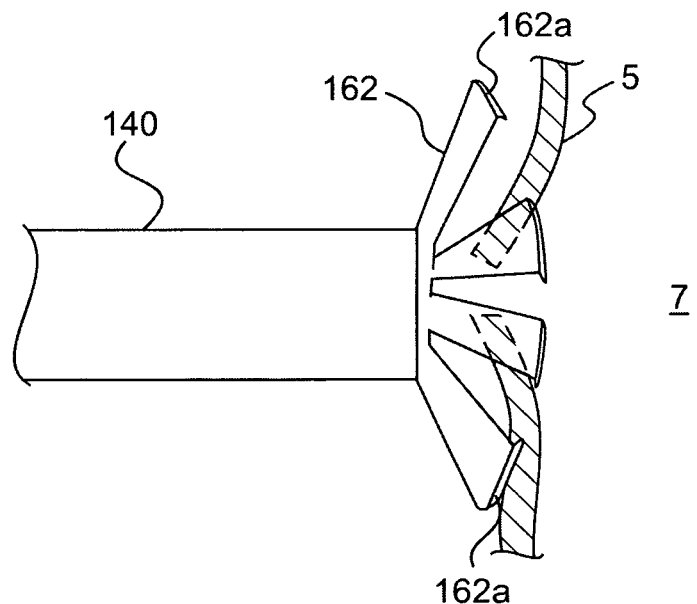

A further embodiment of utilizing retractor 160 to close an aperture 6 in a wall 5 is depicted in FIGS. 10E-10H. In the embodiment of FIGS. 10E-10H, retractor 160 may be disposed in a collapsed configuration about an actuating head 174 having an outer surface 174*d*. Actuating head 174 may include any suitable configuration known in the art. As best shown in FIG. 10G, actuating head 174 may include a generally conical configuration. Actuating head 174 may further include a proximal end 174*a* and a distal end 174*b*. Proximal end 174*a* may generally define an apical portion of the generally conical shape of head 174, and distal end 174*b* may define the basal portion of head 174. In the depicted embodiment, proximal end 174*a* and distal end 174*b* may each include a generally circular cross-sectional configuration.

Furthermore, proximal end 174*a* may be configured to have a cross-sectional diameter that is smaller than the cross-sectional diameter of distal end 174*b*. Moreover, embodiments of actuating head 174 may include a lumen 174*c* disposed therein. Lumen 174*c* may extend the entire length of head 174. In particular, lumen 174*c* may extend from an opening disposed in proximal end 174*a* to an opening disposed in distal end 174*b*. Additionally, lumen 174*c* may include any suitable configuration. In the depicted embodiment, lumen 174*c* may also include a generally conical configuration, with a cross-sectional diameter of lumen 174*c* progressively increasing from proximal end 174*a* to distal end 174*b*. Furthermore, those having ordinary skill in the art will readily recognize that lumen 174*c* may be replaced by two or more lumens having a smaller cross-sectional diameter.

Proximal end 174*a* of actuating head 174 may be mechanically coupled to a distal end 170*a* of push-rod 170. A proximal end (not shown) of push-rod 70 may extend to, for example, handle 101. The proximal end of push-rod 170 may be selectively manipulable to advance or retract push-rod 170 within lumen 141. Push-rod 170 may include any suitable configuration known in the art. Additionally, embodiments of push-rod 170 may include a lumen 178 in fluid communication with lumen 174*c*. While those having ordinary skill in the art will readily appreciate that actuating head 174 and push-rod 170 may be made of a one-piece construction, push-rod 170 and actuating head 174 may be configured as two pieces that are fixedly coupled together. In embodiments, where head 174 and push-rod 170 are formed as two discrete pieces that are later joined together, lumen 178 may be joined to lumen 174*c* in a manner that provides a hermetically sealed junction.

Retractor 160 may be substantially similar to the retractor described in connection with the other embodiments disclosed herein. The retractor 160 of the embodiment of FIGS. 10E-10H, however, may optionally include fingers 162 configured to facilitate grasping of tissue surrounding aperture 6. For example, each of fingers 162 may include a distal portion that is bent radially inward to form a hook-like projection 162*a*. Furthermore, retractor 160 of the embodiment depicted in FIGS. 10E-10H may be retained on actuating head 174 with fingers 162 extending distally from base 161. Fingers 162 may be further configured to selectively splay out away from a longitudinal axis 160, for example, in the direction depicted by arrow 165. For example, each of fingers 162 may include a projection 162*b* disposed on an inner surface of fingers 162, as depicted in FIG. 10G. Projection 162*b* may have any suitable configuration known in the art. For example, projection 162 may include a shape that is substantially complimentary to outer surface 174*d* of actuating head 174.

As shown in FIG. 10E, retractor 160 may be disposed within lumen 141 in a collapsed configuration. Retractor 160 may be advanced to an aperture 6 within a tissue wall 5 for closing aperture 6. Retractor 160 may be advanced out of lumen 141 and toward aperture 6 by selectively advancing push-rod 170 in the direction illustrated by arrow 172 in FIG. 10E. Once completely out of lumen 141 and positioned proximate aperture 6, push-rod 170 may be retracted in the direction illustrated by arrow 176, so as to expand retractor 160. Retracting push-rod 170 in the direction of arrow 176 may cause outer surface 174d to engage projections 162b in a cam-like manner to radially expand retractor 160 by forcing fingers 162 away from a longitudinal axis of retractor 160. Retractor 160 will continue to expand as projections 162b slide along outer surface 174d of conical head 174, reaching maximum expansion as projections 162b approach distal end 174b. As distal end 174b slides proximally past projections 162b, retractor 160, as a result of being formed from a material capable of retaining a preformed shape, such as, for example, a shape memory material or spring steel, will spring back to a collapsed configuration, as hook-like projections 162a grab and collapse the wall around aperture 6 to close aperture 6.

In some instances, the portions of wall 5 surrounding aperture 6 may not be oriented in a manner conducive to collapsing retractor 160 about the wall 5 surrounding aperture 6 for closing aperture 6. In these instances, in may be desirable to draw the portions of wall 5 that surround aperture 6 toward a center portion of retractor 160, to facilitate collapsing retractor 160 on the portions of wall 5 that surround aperture 6. The portions of wall 5 that surround aperture 6 may be drawn toward a center portion of retractor 160 by any suitable means known in the art. For example, sufficient suction may be applied through lumens 178 and 174c to draw the portions of wall 5 that surround aperture 6 toward a center portion of retractor 160.

Once retractor 160 is secured to tissue 5, as shown in, for example, FIG. 10D, elongate member 140 and push-rod 170 may be withdrawn proximally and out of the patient's body. Aperture 6 may then heal and retractor 160 may be left in the body as it is biocompatible or bioresorbable, or may be removed at any point in time using any suitable means.

Figure 13:
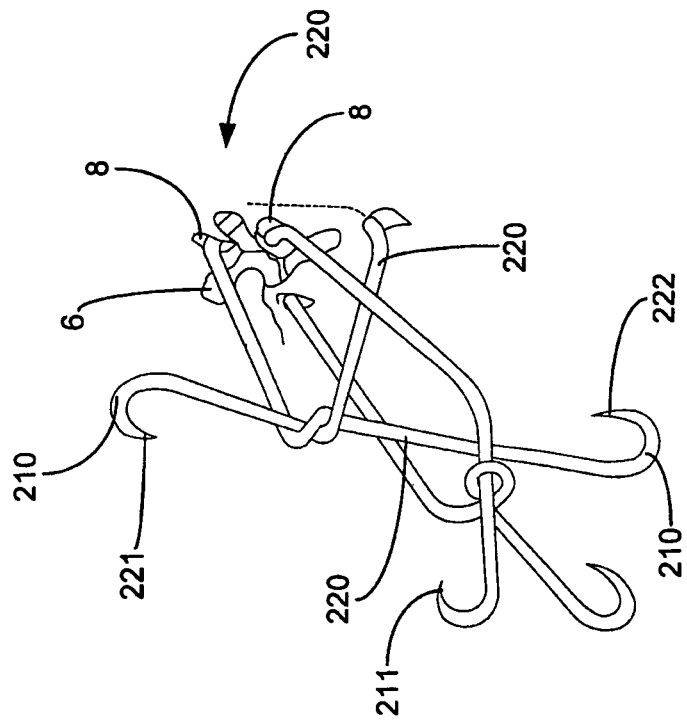
FIGS. 12-13 depict an apparatus and method of using the apparatus, according to a further embodiment of the invention.
Figure 12:
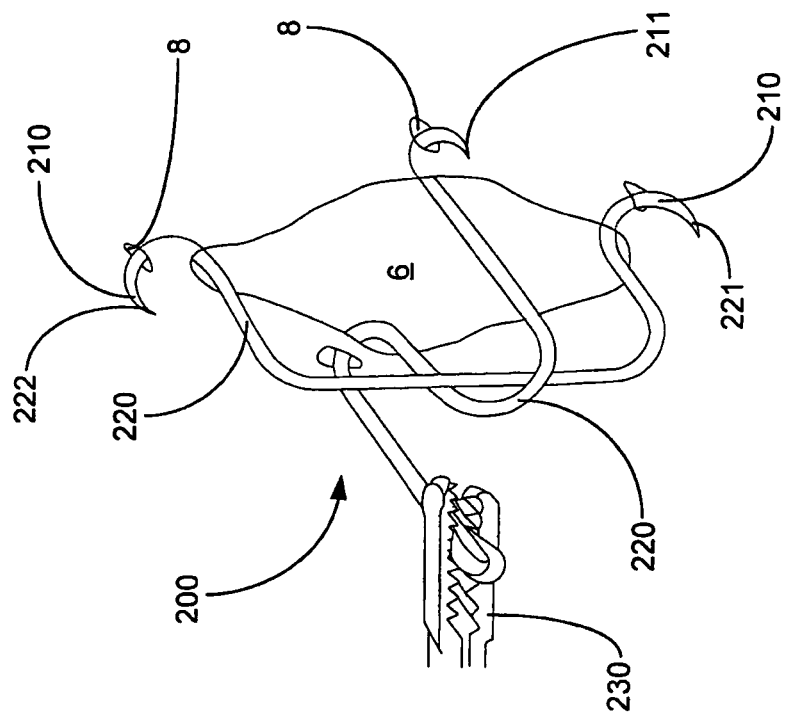

Another embodiment of the invention may include an apparatus 200 configured to close aperture 6, for example, as shown in FIGS. 12-13. Apparatus 200 may include a plurality of hooks 210. Each of hooks 210 may be configured to pierce tissue, for example, via sharp distal end 211. Accordingly, hooks 210 may be configured to be disposed in apertures 8 which are disposed around aperture 6. Apertures 8 may have a smaller cross-sectional area than aperture 6.

At least some of the plurality of hooks 210 may be connected to each other so as to close aperture 6. For example, at least two of hooks 210 may be connected to each other by a flexible elongate member 220. Indeed, hooks 210 may be integrally formed with flexible elongate member 220 such that the ends 221, 222 of flexible elongate member 220 are hooks 210. Hooks 210 on opposite ends 221, 222 of flexible elongate member 220 may be configured to be disposed in apertures 8 on different sides of aperture 6 so as to assist in closing aperture 6. For example, hooks 210 on opposite ends 221, 222 of flexible elongate member 220 may be disposed in apertures 8 on substantially opposite sides of aperture 6.

Hooks 210 may be configured to be manipulated by a user using any suitable method, for example, via jaw 230. Jaw 230 may be used to grab and tie ends 221, 222 of flexible elongate member 220 together and in the process bring apertures 8, on different sides of aperture 6 through which hooks 210 of ends 221, 222 extend, closer together. When two or more flexible elongate members 220 are tied in such a manner so as to bring two or more sets of apertures 8 together, the cross-sectional area of aperture 6 may be reduced and/or closed. Ends 221, 222 of any combination of flexible elongate members 220 may be tied together in any suitable configuration so as to bring apertures 8 closer together and close aperture 6.

Hooks 210 and/or flexible elongate member 220 may be made out of any suitable material(s), for example, any biocompatible material capable of retaining a hook-like configuration for hooks 210. Hooks 210 may be configured to be flexible such that they may take a substantially straight configuration when external force is applied. Hooks 210 may be formed out of a stiffer material or a stiffer version of the same material than the rest of flexible elongate member 220. Hooks 210 and/or flexible elongate member 220 may be configured and/or manufactured to remain in the body for any suitable length of time, for example, until aperture 6 is healed, for example, permanently closed by tissue growth. At that juncture, hooks 210 and/or flexible elongate member 220 may be removed, for example, manually or by being made of a material that may degrade over time.

Another embodiment of the invention may include an apparatus 300 configured to close aperture 6, for example, as shown in FIGS. 14-17, 17A. Apparatus 300 may include a plurality of hooks 310. Each of hooks 310 may be configured to pierce tissue, for example, via sharp distal end 311. Accordingly, hooks 310 may be configured to be disposed in apertures 8 which are disposed around aperture 6. Apertures 8 may have a smaller cross-sectional area than aperture 6. Distal end 311 may include a barb-like configuration.

Figure 15:
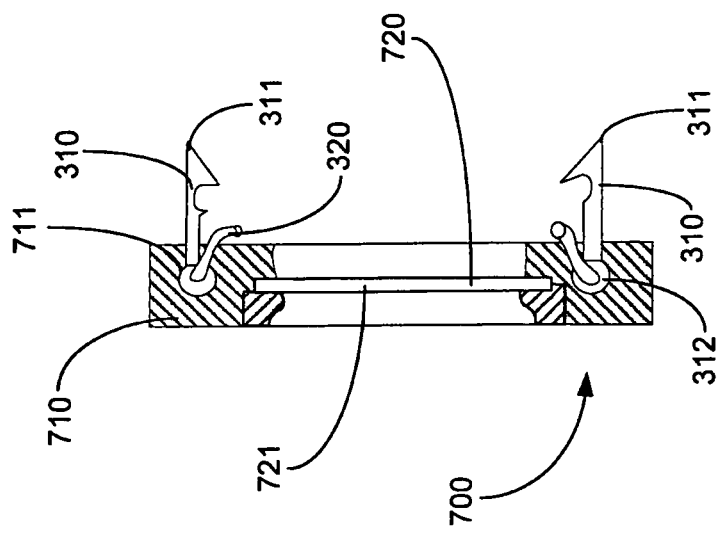

Hooks 310 may each include a connector 312 configured to accommodate a strand 320 therethrough, for example, through an aperture 313. Connector 312 may be separately connected to or integrally formed with hooks 310. Strand 320 may be placed through apertures 313 of hooks 310 in any suitable manner and in any suitable configuration. For example, strand 320 may be placed through alternating connectors 312 (e.g., every other connectors 312) until the last hook 310 is reached, and then strand 320 may be looped back through passed over connectors 312, for example, as shown in FIG. 15. Distal end 321 of strand 320 may then be connected to a portion 320 proximal to distal end 321 and the portions of strand 320 disposed through apertures 313, using any suitable method or mechanism, for example, by tying off distal end 321 around strand 320.

Once hooks 310 are disposed in apertures 8, strand 320 may be pulled taught proximally so as to place pressure on connectors 312 and bring hooks 310 together, for example, as shown in FIG. 17. By doing so, apertures 8 may be brought closer together so as to reduce the cross-sectional area of and/or close aperture 6, for example, as shown in FIG. 17A. Strand 320 may be kept taut so as to ensure hooks 310 remain relatively close together so as to close aperture 6 and allow it to heal. For example, distal end 321 of strand 320 may then be tied off or otherwise affixed to strand 320 so as to prevent proximal or distal movement of distal end 321. The portion of strand 320 proximal to where distal end 321 meets strand 320 may then be removed. Hooks 310 and/or strand 320 may be configured and/or manufactured to remain in the body for any suitable length of time, for example, until aperture 6 is healed (e.g., permanently closed by tissue growth). At that juncture, hooks 310 and/or strand 320 may be removed, for example, manually or by being made of a material that may degrade over time.

Figure 14:
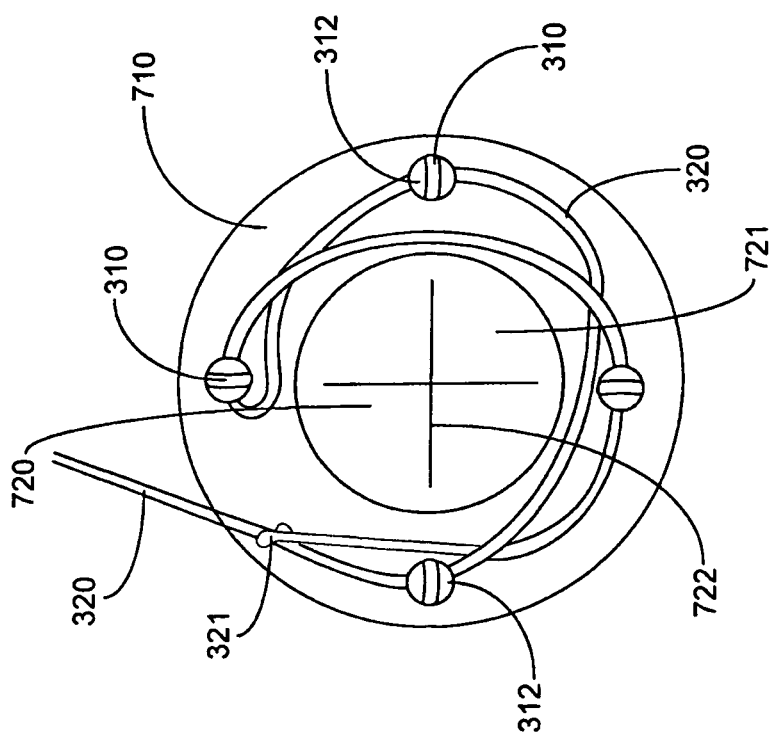

Still another embodiment of the invention may include apparatus 700, for example, as shown in FIGS. 14-16. Apparatus 700 may be configured to deploy one or more devices configured to close aperture 6, for example, apparatus 300, which includes hooks 310 and strand 320. For exemplary purposes only, apparatus 700 will be described in conjunction with the use of apparatus 300, however, apparatus 700 is an optional additional structure for use in conjunction with any suitable apparatus set forth herein for closing aperture 6.

Apparatus 700 may include an outer ring 710 and an inner member 720. Inner member 720 may be a gastric port including a septum 721 defining a perforation 722. Septum 721 and perforation 722 may be configured to accommodate a medical device therethrough and/or fluid flow therethrough with sufficient suction or fluid pressure force. Otherwise, septum 721 remains closed to prevent undesirable passage of material across aperture 6 during the medical procedure. Apparatus 700 including outer ring 710 may be made of a flexible material configured to fold, for example, such that apparatus 700 can fit into a lumen having a cross-sectional area smaller than that of apparatus 700. Accordingly, apparatus 700 would be advanced into GI tract 3 in such a lumen in a folded state, and once the appropriate area was reached, apparatus 700 could be advanced out of the lumen where it could expand into the shape shown in FIGS. 14-16.

Outer ring 710 may include a plurality of apertures 711. Each of apertures 711 may be configured to accommodate at least one hook 310 therethrough. For example, connector 312 of hooks 310 may be press-fit into apertures 711, such that each of hooks 310 may be selectively detached from apertures 711 in outer ring 710. Outer ring 710 may be configured such that apertures 711 are deployed about outer ring 710 so as to be able to place hooks 310 in wall 5 around aperture 6. In such embodiments, septum 721 and perforation 722 may be roughly aligned with aperture 6. Once hooks 310 have been placed in aperture 8 of wall 5 (e.g., by advancing hooks 310 through wall 5), apparatus 700 may be advanced away from wall 5 while leaving hooks 310 retained in wall 5. A combination of hooks 310 placing a distal pressure on connector 312 (e.g., due to being embedding in wall 5) and outer ring 710 moving proximally relative to wall 5 may allow connectors 312 to advance out of aperture 711. Accordingly, connector 312 and/or strand 320 may pass through aperture 711. Strand 320 may then be used to pull hooks 310 closer together so as to close aperture 6 using any method or mechanism set forth herein.

Figure 18:
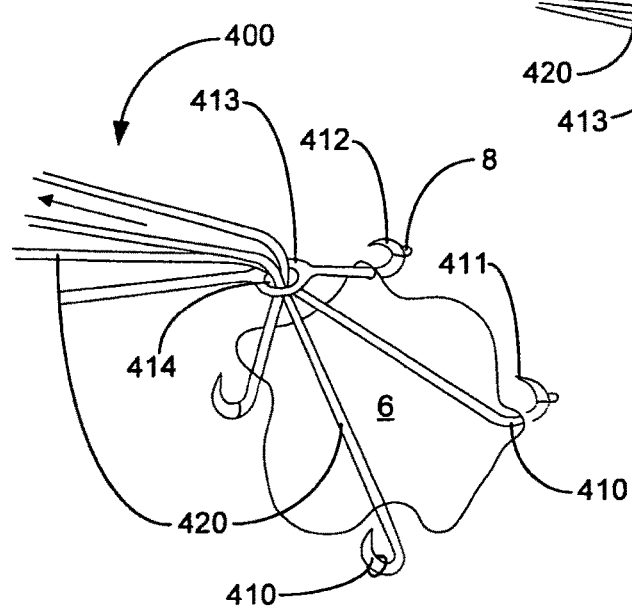
FIGS. 18-20 depict an apparatus and method of using the apparatus, according to a yet further embodiment of the invention.
Figure 19:
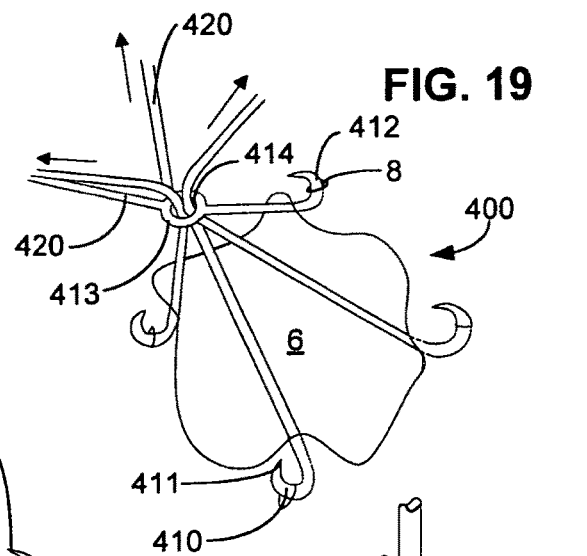
Figure 20:
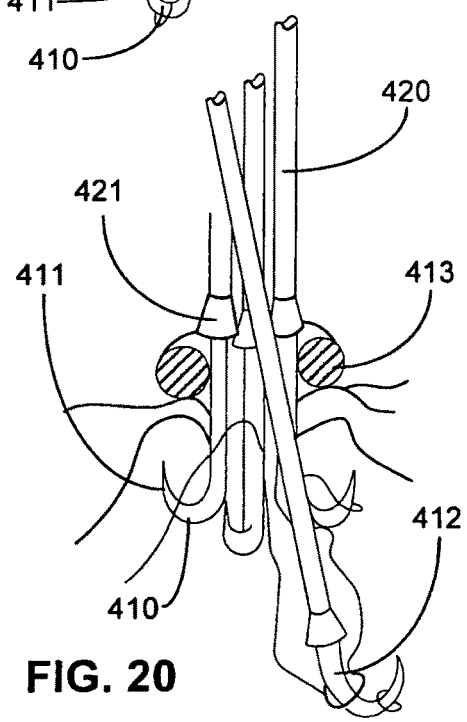

A further embodiment of the invention may include an apparatus 400 configured to close aperture 6, for example, as shown in FIGS. 18-20. Apparatus 400 may include a plurality of hooks 410. Each of hooks 410 may be configured to pierce tissue, for example, via sharp distal end 411. Accordingly, hooks 410 may be configured to be disposed in apertures 8 which are disposed around aperture 6. Apertures 8 may have a smaller cross-sectional area than aperture 6.

At least some of the plurality of hooks 410 each may be connected to a corresponding flexible elongate member 420. Indeed, hooks 410 may be integrally formed with flexible elongate member 420 such that a distal end of each flexible elongate member 420 is one of hooks 410. Hooks 410 may be disposed in apertures 8 disposed on different sides of aperture 6. One of hooks 412 may include a connector 413 configured to engage the elongate members of other hooks 410, for example, one or more flexible elongate members 420 may be placed through an aperture 414 of connector 413 of hook 412.

Once hooks 410, 412 have been deployed in apertures 8, one or more flexible elongate members 420 at least a portion of which are disposed in aperture 414, may be pulled in a proximal direction. The one or more flexible elongate members 420 may be pulled together in substantially the same direction, or may be pulled separately in different directions. Flexible elongate members 420 may be pulled in the proximal direction until hooks 410 are substantially disposed in or substantially immediately adjacent to aperture 414. In such a manner, apertures 8 may be brought together so as to cause aperture 6 to close. One or more collars 421 may then be placed around at least some of flexible elongate members 420 immediately proximal to aperture 414, for example, to keep apertures 8 close together and aperture 6 closed.

Hooks 410 and/or flexible elongate member 420 may be made out of any suitable material(s), for example, any biocompatible material capable of retaining a hook-like configuration for hooks 410. Hooks 410 may be configured to be flexible such that they may take a substantially straight configuration when external force is applied. Hooks 410 may be formed out of a stiffer material or a stiffer version of the same material than the rest of flexible elongate member 420. Hooks 410 and/or flexible elongate members 420 may be configured and/or manufactured to remain in the body for any suitable length of time, for example, until aperture 6 is healed, for example, permanently closed by tissue growth. At that juncture, hooks 410 and/or flexible elongate members 420 may be removed, for example, manually or by being made of a material that may degrade over time.

Figure 21:
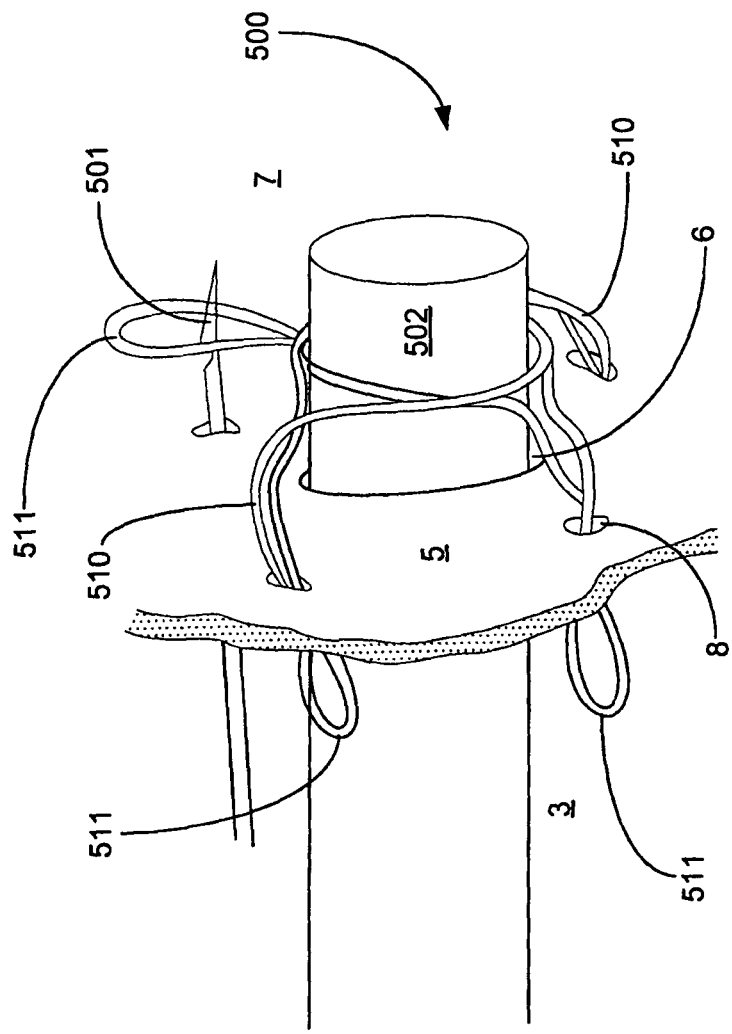
FIGS. 21-23 depict an apparatus, a tool for use with the apparatus, and methods of using both the tool and the apparatus, according to still another embodiment of the invention.
Figure 23:
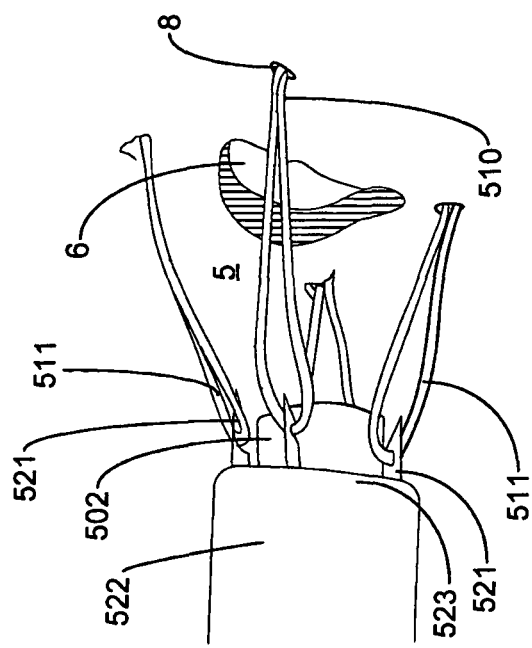
Figure 22:
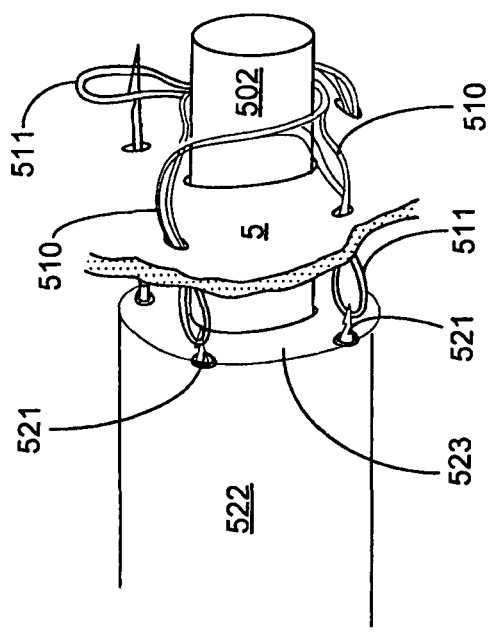

Yet another embodiment of the invention includes apparatus 500, for example, as shown in FIGS. 21-23. Apparatus 500 may include a strand 510. Strand 510 may include a plurality of loops 511 (e.g., square knot loops). Strand 510 may be deployed in GI tract 3, through wall 5 via aperture 6, and/or body cavity 7 using any suitable device and/or method, for example, via a distal end of tubular member 502. Strand 510 may be attached to an exterior of tubular member 502 during deployment in a preformed configuration, for example, already including square knot loops 511. In such a preformed configuration, loops 511 may be ready to be deployed into apertures 8. Strand 510 may be attached to the distal end of tubular member 502 in such a preformed configuration using adhesives.

In another example, strand 510 may be disposed in a lumen of tubular member 502 in the preformed configuration including loops 511 (e.g., square knot loops). In the preformed configuration, strand 510 may already substantially have the shape with which it is to be deployed within wall 5. Such a preformed configuration may be maintained, for example, by using adhesives so as to attach strand 510 to the inner wall of the lumen of tubular member 502. To that end, strand 510 may be made of a semi-rigid material or be coated with a semi-rigid material (for example, a wax-like substance, stiff filament, nitinol) such that strand 510 can generally keep the preformed configuration unless directly manipulated.

Strand 510 may be configured such that loops 511 may be placed through one or more apertures 8 using any suitable method, for example, manually or using a device such as hook 501. Apertures 8 may be formed using hook 501. Loops 511 may be disposed on one side of wall 5 while the rest of strand 510 may be disposed on the other. Loops 511 may be pulled in a direction away from wall 5 so as to cause the rest of strand on the opposite side of wall 5 to come together so as to cause apertures 8 to come together and substantially close aperture 6. Loops 511 may be pulled using any suitable mechanism or method, for example, manually or via one or more hooks 521 disposed on a distal end 523 of an elongate member 522. Elongate member 522 may surround tubular member 502. Once aperture 6 has been sufficiently closed, loops 511 may be tied off and/or twisted together using any suitable mechanism or method. Strand 510 may be configured and/or manufactured to remain in the body for any suitable length of time, for example, until aperture 6 is healed (e.g., permanently closed by tissue growth). At that juncture, strand 510 may be removed, for example, manually or by being made of a material that may degrade over time.

In various embodiments, strand 510 may include a plurality of strands. Strand 510 also may not be continuous loops, but have ends which either may be tied together or left apart if leaving them apart does not affect the deployment of strand 510 in closing aperture 6.

Figure 24:
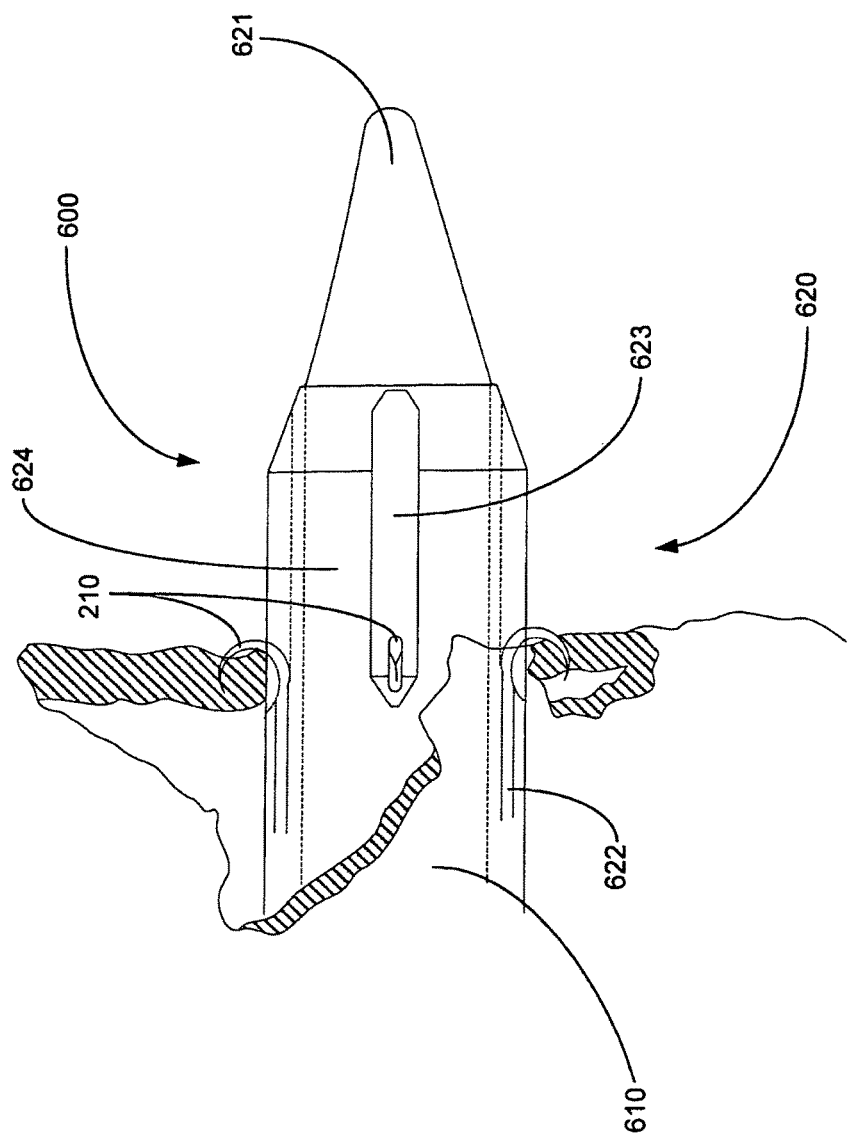
FIG. 24 depicts a tool for use with the apparatus set forth in FIGS. 12-13, according to a still further embodiment of the invention.

A yet further embodiment of the invention may include apparatus 600, for example, as shown in FIG. 24. Apparatus 600 may be configured to deploy one or more devices configured to close aperture 6, for example, apparatus 200 including hooks 210 and/or apparatus 400 including hooks 410. For exemplary purposes only, apparatus 600 will be described in conjunction with the use of apparatus 200, however, apparatus 600 may be used in conjunction with any suitable apparatus set forth herein for closing aperture 6.

Apparatus 600 may include an elongate member 610 and a distal assembly 620. Elongate member 610 may be configured to be advanced through a body lumen, for example, GI tract 3. Distal assembly 620 may include a distal end 621 configured to pierce tissue and/or form aperture 6. Distal assembly 620 may also include interior channels 622, each channel 622 in flow communication with a corresponding slot 623 disposed on exterior surface 624 of distal assembly 620. Interior channels 622 may be configured to accommodate at least one hook 210. The portion of distal assembly 620 defining interior channels 622 may be configured to place pressure on hooks 210, for example, so as to force hooks 210 to be disposed in a substantially straight configuration when substantially the entirety of hooks 210 are disposed in interior channels 622. Interior channels 622 and/or slots 623 may be disposed about distal assembly 620 in any suitable configuration, for example, they may be substantially regularly spaced circumferentially about distal assembly 620.

After distal assembly 600 has been placed through aperture 6, slots 623 may be placed adjacent to wall 5 around aperture 6. Hooks 210 disposed in interior channels 622 may then be advanced distally using any suitable mechanism or method such that as distal end 211 emerges from slot 623, hook 210 curves and enters wall 5 to form apertures 8. In the alternative, aperture 8 may be preformed prior to placement of distal end 211 of hook 210 in aperture 8. Once hooks 210 have been deployed in apertures 8, distal assembly 620 may be removed, for example, proximally from aperture 6 and GI tract 3, leaving hooks 210 in place. Flexible elongate member 220 and hook 210 on the opposite end of flexible member 220 may also be disposed in interior channels 622 and may also be deployed in GI tract 3 via slots 623. The other hook 210 may then be manipulated and placed through an aperture 8 on substantially the opposite side of aperture 6 from the first hook 210. Apparatus 210 may then be manipulated using any method and mechanism set forth herein so as to deploy hook(s) 210 in apertures 8 and close aperture 6.

A further embodiment of the invention may include a method of closing aperture 6 using a combination of apparatus 600 and apparatus 200, for example, as shown in FIGS. 12, 13, and 24. For example, apparatus 600 may be advanced through GI tract 3 until distal end 621 of distal assembly extends through aperture 6. Slots 623 may be disposed on the same side of wall 5 as distal end 621. Hooks 210, disposed in interior channels 622 in a substantially straight configuration, may be advanced distally through slots 623 such that they regain their natural curvature when they exit slots 623. Flexible elongate member 220 and hook 210, disposed on the other end of flexible elongate member 220 from hook 210 being deployed into aperture 8 from slot 623, may also be disposed in interior channel 622 proximal to slot 623, and may be deployed into GI tract 3 once hook 210 is disposed in aperture 8. Each distal end 211 may penetrate wall 5 at an aperture 8. When hooks 210 are sufficiently embedded in wall 5, apparatus 600 may be removed proximally from body cavity 7, aperture 6, and GI tract 3, leaving apparatus 200. Ends 221, 222 of flexible elongate member 220 may include hooks 210. Ends 221, 222 may then be manipulated, for example, via jaws 230, so as to pull ends 221, 222 back through wall 5 and into GI tract 3. In doing so, flexible elongate member 220 may be pulled through apertures 8, bringing different apertures 8 closer together so as to close aperture 6. When aperture 6 is sufficiently closed, ends 221, 222 may be tied together or restricted in some other way so as to keep aperture 6 closed. This may be repeated for as many apparatuses 200 that are deployed by apparatus 600. Aperture 6 may then be left to heal, and apparatuses 200 may remain in wall 5 until they are removed using any suitable method at the desired time, for example, manually or because apparatus 200 is made of a material that degrades over time.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An assembly comprising:
    an apparatus for collapsing an aperture in a wall of tissue, the apparatus including:
        a base spring-biased to collapse into a collapsed state from an expanded state;
        a plurality of collapsible fingers extending from the base, each finger having a connected end connected to the base and a free end opposite the connected end, wherein the free ends are closer together in the collapsed state than in the expanded state, and the connected ends are closer together in the collapsed state than in the expanded state,
        wherein the collapsible fingers are configured to collapse about tissue adjacent to and defining the aperture by pivoting towards each other so as to close the aperture in the wall of tissue; and
    a delivery apparatus, the delivery apparatus including:
        an elongate flexible member, and
        a conical distal assembly connected to the elongate flexible member,
        wherein the distal assembly is configured to accommodate the apparatus, and includes at least one strand connecting the base to the distal assembly, the at least one strand being configured to assist in positioning the apparatus about the aperture to be closed.

2. The apparatus of claim 1, wherein the base defines a gap in the expanded state, and the base is without the gap in the collapsed state.

3. The assembly of claim 1, wherein the base defines an aperture for receiving the distal assembly therethrough.

4. The assembly of claim 1, wherein the distal assembly includes a distal tip configured to puncture the wall of tissue and form the aperture.

5. The assembly of claim 1, wherein the distal assembly includes a member and a stepped portion configured to accommodate the base, wherein a cross-sectional area of the stepped portion is larger than a cross-sectional area of the member immediately proximal to the stepped portion.

6. The assembly of claim 5, wherein an outer surface of the base lies substantially flush with a surface of the distal assembly that is distal to the stepped portion.

7. The assembly of claim 1, wherein a distal end of the elongate member includes a notch configured to accommodate the at least one strand therethrough, wherein the notch is configured to allow the at least one strand to assist in deploying the base about the distal end of the elongate member.

8. The apparatus of claim 1, wherein at least a portion of the base is configured to overlap with another portion of the base, and wherein at least some of the plurality of collapsible fingers are configured to overlap others of the plurality of collapsible fingers.

9. The apparatus of claim 1, wherein the base includes a proximal end, a distal end, and a longitudinal axis extending from the proximal end to the distal end, and the plurality of collapsible fingers are configured to collapse towards the longitudinal axis to press tissue between the plurality of collapsible fingers to close the aperture in the collapsed state.

10. The apparatus of claim 9, wherein the base includes a lumen extending from the proximal end of the base to the distal end of the base, the base being inwardly biased to collapse the lumen radially from the expanded state to the collapsed state to press tissue located within the lumen to close the aperture.

11. The apparatus of claim 10, wherein the base includes two adjacent ends that extend from the lumen to an outer surface of the base, the region between the ends defining a gap that is larger in the expanded state than in the collapsed state.

12. The apparatus of claim 11, wherein the base is radially expandable from the collapsed state to the expanded state and the outer surface encompasses a cross-sectional area in the expanded state that is greater than a cross-sectional area encompassed by the outer surface in the collapsed state.

13. The apparatus of claim 9, wherein each of the plurality of collapsible fingers includes a distal end coupled to the proximal end of the base.

14. The apparatus of claim 1, wherein the free ends of the fingers terminate at blunt tips.

15. An assembly for delivering an apparatus for closing an aperture in a wall of tissue, comprising:
    an elongate flexible member having a proximal portion, a distal portion, and a lumen extending between the proximal portion and the distal portion; and
    a distal assembly connected to the distal portion of the elongate flexible member, wherein the distal assembly includes a distal tip having a stepped portion with a proximal-facing surface connected to a radially-outward-facing surface, each of the surfaces configured to detachably receive the apparatus, and wherein the distal tip is configured to invert during delivery of the apparatus.

16. The assembly of claim 15, wherein the apparatus is disposed about the distal assembly.

17. The assembly of claim 15, wherein the apparatus includes a base and a plurality of collapsible fingers extending from the base.

18. The assembly of claim 17, wherein the apparatus is configured to move between collapsed and expanded configurations.

19. The assembly of claim 17, wherein the base includes a proximal end, a distal end, and a longitudinal axis extending from the proximal end to the distal end, and the plurality of collapsible fingers are configured to collapse towards the longitudinal axis to press tissue between the plurality of collapsible fingers to close the aperture.

20. The assembly of claim 19, wherein the base includes a lumen extending from the proximal end of the base to the distal end of the base, the base being inwardly biased to collapse the lumen radially from the expanded state to the collapsed state to press tissue located within the lumen to close the aperture.

21. The assembly of claim 20, wherein the base includes two adjacent ends that extend from the lumen to an outer surface of the base, the region between the ends defining a gap that is larger in the expanded state than in the collapsed state.

22. The assembly of claim 21, wherein the outer surface encompasses a cross-sectional area in the expanded state that is greater than a cross-sectional area encompassed by the outer surface in the collapsed state.

23. The assembly of claim 19, wherein each of the plurality of collapsible fingers includes a distal end coupled to the proximal end of the base.

24. The assembly of claim 17, wherein each of the plurality of collapsible fingers includes an end rigidly attached to the base.

25. The assembly of claim 15, wherein the distal tip is configured to pierce tissue.

26. An assembly for delivering an apparatus for closing an aperture in a wall of tissue, comprising:
    an elongate flexible member having a proximal portion, a distal portion, and a lumen extending between the proximal portion and the distal portion and having a distal opening;
    a member having a longitudinal axis, a proximal portion, and a distal portion slidably disposed within the lumen of the elongate flexible member;
    an annular apparatus having a circular base and a plurality of fingers, the base and the plurality of fingers surrounding a circumference of the distal portion of the member, each finger having a connected end connected to the base and a free end opposite the connected end, wherein the annular apparatus is retained within the lumen of the elongate flexible member in a collapsed configuration with a free end of each finger positioned farther from the distal opening than the connected end, and wherein the fingers are configured to partially expand away from the longitudinal axis to an expanded configuration to receive tissue adjacent to the aperture when the annular apparatus is advanced out of the distal opening of the lumen of the elongate flexible member and biased to move toward the longitudinal axis to capture the received tissue and close the aperture, wherein movement of the fingers toward the longitudinal axis includes pivoting of the fingers toward the longitudinal axis; and
    an actuator for expanding the fingers of the apparatus from the collapsed configuration to the expanded configuration.

27. A system for closing an aperture in a wall of tissue, comprising:
    an elongate member having a proximal portion, a distal portion, and a lumen extending therebetween;
    an annular apparatus for closing the aperture, mounted about the distal portion of the elongate member, wherein the annular apparatus is configured to move between a first delivery configuration and a second deployed configuration to receive tissue about the aperture, the annular apparatus defines an annulus that is larger in the second deployed configuration than in the first delivery configuration, the apparatus is spring-biased to collapse from the second deployed configuration to a collapsed configuration about the tissue to close the aperture, wherein the annulus is larger in the first delivery configuration than in the collapsed configuration, and wherein the apparatus includes a base and a plurality of fingers extending from the base, wherein the base includes:
a proximal end, a distal end, and a longitudinal axis extending from the proximal end to a distal end, and the plurality of collapsible fingers are configured to collapse towards the longitudinal axis to press tissue between the plurality of collapsible fingers to close the aperture,
a lumen extending from the proximal end of the base to the distal end of the base, the base being inwardly biased to collapse the lumen radially from the expanded configuration to the collapsed configuration to press tissue located within the lumen to close the aperture, and
two adjacent ends that extend from the lumen to an outer surface of the base, the region between the ends defining a gap that is larger in the expanded configuration than in the collapsed configuration; and
an actuator for moving the apparatus from the first delivery configuration to the second deployed configuration.

28. The system of claim 27, wherein the outer surface encompasses a cross-sectional area in the expanded configuration that is greater than a cross-sectional area encompassed by the outer surface in the collapsed configuration.

29. An apparatus, comprising:
an annular base having an aperture therein, an end, and a central axis, wherein the aperture lies in a plane, and the central axis extends through the aperture in a direction perpendicular to the plane, and wherein the annular base is spring-biased to move from an expanded configuration to a collapsed configuration, the annular base being larger in the expanded configuration than in the collapsed configuration; and
a plurality of fingers projecting from the end of the annular base alongside the central axis, wherein the fingers are biased to move toward the central axis by pivoting toward the central axis from the expanded configuration to the collapsed configuration to close the aperture,
wherein the base includes a lumen extending from a proximal end of the base to a distal end of the base, the base being inwardly biased to collapse the lumen radially from the expanded configuration to the collapsed configuration to press tissue located within the lumen to close the aperture, and
wherein the base includes two adjacent ends that extend from the lumen to an outer surface of the base, the region between the ends defining a gap that is larger in the expanded configuration than in the collapsed configuration.

30. The apparatus of claim 29, wherein the outer surface encompasses a cross-sectional area in the expanded configuration that is greater than a cross-sectional area encompassed by the outer surface in the collapsed configuration.

31. An apparatus for compressing tissue about an aperture in a wall of tissue, comprising:
an annular base inwardly biased to move from an expanded state to a collapsed state, wherein the annular base in the collapsed state includes a proximal end, a distal end, an expandable lumen, and an outer surface, the annular base further including a gap extending between the proximal end, the distal end, the lumen, and the outer surface, the gap being greater in the expanded state than the collapsed state; and
a plurality of fingers extending from the annular base, wherein each of the fingers is rigidly coupled to the annular base at a connected end, each of the fingers has a blunt tip opposite the connected end, the fingers are configured to move with the annular base between the expanded state and the collapsed state to compress tissue located between the plurality of fingers, and movement of the fingers with the annular base includes radially inward pivoting of the fingers toward a longitudinal axis of the annular base.

32. The apparatus of claim 31, wherein the longitudinal axis extends from the proximal end to the distal end and the plurality of fingers are configured to collapse towards the longitudinal axis to press tissue between the plurality of fingers to close the aperture.

33. The apparatus of claim 32, wherein the plurality of fingers are biased to collapse towards the longitudinal axis.

34. The apparatus of claim 31, wherein the base is inwardly biased to collapse the lumen radially from the expanded state to the collapsed state to press tissue located within the lumen to close the aperture.

35. The apparatus of claim 31, wherein the outer surface encompasses a cross-sectional area in the expanded state that is greater than a cross-sectional area encompassed by the outer surface in the collapsed state.

36. The apparatus of claim 31, wherein each of the plurality of fingers includes a distal end coupled to the proximal end of the base.

37. An apparatus for compressing tissue about an aperture in a wall of tissue, comprising:
a conical base structure inwardly biased to move from an expanded state to a collapsed state, wherein the conical base structure includes a proximal aperture, a distal aperture, a lumen extending from the proximal aperture to the distal aperture, and a wall at least partially surrounding the lumen, the conical base structure further including a gap in the wall, the gap being greater in the expanded state than the collapsed state; and
a plurality of fingers extending from the conical base structure, wherein each of the fingers is coupled to the conical base structure at a connected end, each of the fingers has a substantially flat tip opposite the connected end, the fingers are configured to move with the conical base structure between the expanded state and the collapsed state to compress tissue located between the plurality of fingers, and movement of the fingers with the conical base structure includes a radially inward pivoting of the fingers toward a longitudinal axis of the conical base structure.

38. The apparatus of claim 37, wherein the distal aperture is smaller than the proximal aperture.

39. The apparatus of claim 37, wherein the gap extends from a proximal end of the wall to a distal end of the wall.

40. The apparatus of claim 37, wherein the base includes a proximal end, a distal end, the longitudinal axis extends from the proximal end to the distal end, and the plurality of fingers are configured to collapse towards the longitudinal axis in the compressed state.

41. The apparatus of claim 40, wherein the base is inwardly biased to collapse the lumen radially from the expanded state to the collapsed state to press tissue located within the lumen to close the aperture.

42. The apparatus of claim 41, wherein the base includes two adjacent ends that extend from the lumen to an outer surface of the base, the region between the ends defining the gap.

43. The apparatus of claim 42, wherein the outer surface encompasses a cross-sectional area in the expanded state that is greater than a cross-sectional area encompassed by the outer surface in the collapsed state.

44. The apparatus of claim 37, wherein each of the plurality of fingers includes a distal end coupled to a proximal end of the base.

* * * * *